(12) United States Patent
Wada

(10) Patent No.: US 9,364,826 B2
(45) Date of Patent: Jun. 14, 2016

(54) TEST CHIP AND TEST CHIP UNIT INCORPORATED WITH TEST CHIP

(75) Inventor: Shigeru Wada, Kishiwada (JP)

(73) Assignee: KONICA MINOLTA, INC (JP)

( * ) Notice: Subject to any disclaimer, the term of this patent is extended or adjusted under 35 U.S.C. 154(b) by 353 days.

(21) Appl. No.: 13/982,666

(22) PCT Filed: Jan. 18, 2012

(86) PCT No.: PCT/JP2012/000276

§ 371 (c)(1),
(2), (4) Date: Jul. 30, 2013

(87) PCT Pub. No.: WO2012/105171

PCT Pub. Date: Aug. 9, 2012

(65) Prior Publication Data

US 2013/0312546 A1 Nov. 28, 2013

(30) Foreign Application Priority Data

Jan. 31, 2011 (JP) .................................. 2011-018303

(51) Int. Cl.
*G01N 21/75* (2006.01)
*B01L 3/02* (2006.01)
(Continued)

(52) U.S. Cl.
CPC ........... *B01L 3/021* (2013.01); *B01L 3/502715* (2013.01); *G01N 21/05* (2013.01); *G01N 21/648* (2013.01); *G01N 33/48707* (2013.01); *G01N 35/1079* (2013.01); *B01L 3/0275* (2013.01);
(Continued)

(58) Field of Classification Search
CPC . B01L 3/021; B01L 3/502715; B01L 3/0275; B01L 2200/027; B01L 2200/0689; B01L 2300/044; B01L 2300/0636; B01L 2300/0877; B01L 2400/0487; G01N 21/05; G01N 21/648; G01N 33/48707; G01N 35/1079; G01N 2021/058; G01N 2035/00158
See application file for complete search history.

(56) References Cited

U.S. PATENT DOCUMENTS

2010/0028985 A1 2/2010 Hanafusa et al.

FOREIGN PATENT DOCUMENTS

JP 3660006 B2 3/2005
JP 2005315685 A * 11/2005
(Continued)

OTHER PUBLICATIONS

International Search Report for International Application No. PCT/JP2012/000276; Mailing Date Mar. 19, 2012, with English Translation.

(Continued)

*Primary Examiner* — Dennis M White
(74) *Attorney, Agent, or Firm* — Cantor Colburn LLP

(57) ABSTRACT

The present invention discloses an arrangement provided with a chip body having a fluid channel and configured such that an end portion of the fluid channel is opened in a surface of the chip body, and a sheet-like seal member which covers at least the opening in the surface of the chip body for bringing the inside of the fluid channel to a sealed state. The seal member is constituted of laminated sheet members including a first sheet member having a ductility and an elasticity capable of forming a hole therein with use of a nozzle member, and a second sheet member having a lower ductility than the first sheet member. The sheet members adjoining each other are adhered to each other by an adhesive or a tackifier. The second sheet member is disposed on the chip body side than the first sheet member.

16 Claims, 10 Drawing Sheets

(51) Int. Cl.
  *G01N 33/487* (2006.01)
  *G01N 35/10* (2006.01)
  *B01L 3/00* (2006.01)
  *G01N 21/05* (2006.01)
  *G01N 21/64* (2006.01)
  *G01N 35/00* (2006.01)

(52) U.S. Cl.
  CPC .... *B01L 2200/027* (2013.01); *B01L 2200/0689* (2013.01); *B01L 2300/044* (2013.01); *B01L 2300/0636* (2013.01); *B01L 2300/0877* (2013.01); *B01L 2400/0487* (2013.01); *G01N 2021/058* (2013.01); *G01N 2035/00158* (2013.01)

(56) References Cited

FOREIGN PATENT DOCUMENTS

| | | | |
|---|---|---|---|
| JP | 2009281954 A | * | 12/2009 |
| WO | 2006104213 A1 | | 10/2006 |

OTHER PUBLICATIONS

Written Opinion of the International Searching Authority for International Application No. PCT/JP2012/000276, with English Translation.

* cited by examiner

TEST CHIP AND TEST CHIP UNIT INCORPORATED WITH TEST CHIP

CROSS REFERENCE TO RELATED APPLICATIONS

This is the U.S. national stage of application No. PCT/JP2012/000276, filed on 18 Jan. 2012. Priority under 35 U.S.C. §119(a) and 35 U.S.C. §365(b) is claimed from Japanese Application No. 2011-018303, filed 31 Jan. 2011, the disclosure of which is also incorporated herein by reference.

TECHNICAL FIELD

The present invention relates to a test chip configured such that a hole is formed in a seal member for injecting and sucking a test solution in and out of a fluid channel having an end opening thereof sealed by the seal member, and a test chip unit incorporated with the test chip; and more particularly to a test chip to be used in a biochemical test, and a test chip unit incorporated with the test chip.

BACKGROUND ART

Conventionally, there has been known a test chip for use in DNA analysis, biochemical tests and the like, as disclosed in patent literature 1. As shown in FIGS. 12A and 12B, the test chip is provided with a chip body 110 in the form of a flat plate, a reservoir part 112 for storing a test solution such as a reagent, and a reaction part 114 for reacting the test solution stored in the reservoir part 112 with a sample or the like. The reservoir part 112 is provided with reservoir concave parts 112a, and a seal member 112b in the form of a sheet. The reservoir concave parts 112a are formed in the upper surface of the chip body 110, and are recessed downwardly. The seal member 112b is attached to the upper surface of the chip body 110 in such a manner as to cover the upper openings of the reservoir concave parts 112a in a state that a test solution is stored in the reservoir concave parts 112a.

In the thus-configured test chip 100, at first, a sample and the like are placed on the reaction part 114. Then, a hole is formed in the seal member 112b with use of a nozzle member 116 (see FIG. 12B), and the test solution in the reservoir concave parts 112a is sucked with use of the nozzle member 116. The sucked test solution is ejected onto the reaction part 114, on which the sample is placed, with use of the nozzle member 116. By the above operation, the sample and the test solution are mixed and reacted with each other. Then, a test result is obtained based on the reaction.

The seal member 112b of the test chip 100 is a member for use in preventing vaporization of the test solution from the reservoir concave parts 112a and intrusion of foreign matter into the test solution until the sample is tested with use of the test chip 100. Therefore, it is unknown whether adhesion (sealability) between the nozzle member 116 and the seal member 112b is sufficiently obtained during a period of time when the nozzle member 116 is inserted through the seal member 112b for injecting or sucking the test solution in and out of the reservoir concave parts 112a. In view of the above, liquid leakage from between the nozzle member 116 and the seal member 112b should be taken into consideration, when the inner pressure of the reservoir concave parts 112a is greatly fluctuated during an operation of sucking and injecting the test solution in and out of the reservoir concave parts 112a with use of the nozzle member 116 inserted through the seal member 112b.

As disclosed in patent literature 2, there is known a seal member for use in sealing a straw insertion hole of a paper beverage container, as a seal member taking into consideration of adhesion between a nozzle member and the seal member when the nozzle member is inserted through the seal member, for instance. As shown in FIG. 13, the seal member is configured such that an insertion hole periphery 210 of a straw insertion hole 211 of a paper beverage container is held between an inner film 212 disposed on the inner side of the insertion hole periphery 210, and an outer film 214 disposed on the outer side of the insertion hole periphery 210. In this state, portions of the inner film 212 and the outer film 214 corresponding to the straw insertion hole 211 are adhered to each other by thermal adhesion. The outer film 214 is a polymer film. The inner film 212 is formed by laminating an aluminum sheet 216 and a polymer film 218 one over the other by thermal adhesion.

In the thus configured seal member 200, when a straw is inserted into the paper beverage container through the seal member 200 via the straw insertion hole 211 by pressing a sharp end of the straw against the seal member 200, adhesion is secured between the outer circumferential surface of the straw and a periphery of the opening (opening formed by inserting the straw) of the seal member 200. Thus, there is no likelihood that the contents (beverage) in the paper beverage container may leak from between the outer circumferential surface of the straw and the opening periphery of the seal member 200.

However, since the films 214, 216, and 218 constituting the seal member 200 are adhered to each other by thermal adhesion, the adhesion force between the films 214, 216, and 218 is weak. Accordingly, if the inner pressure fluctuation of the paper beverage container is repeated, or an operation of inserting and taking out a straw is repeated, the films 214, 216, and 218 may be peeled off from the opening periphery of the seal member 200. This peeling-off phenomenon gradually spreads. If the peeling-off phenomenon of the films 214, 216, and 218 constituting the seal member 200 spreads as described above, liquid leakage may occur from the peeled portions. As a result, even if the seal member 200 of the paper beverage container is used to seal the fluid channel or the reservoir concave parts of the test chip 100, liquid leakage may occur by pealing off of the films from each other, as the inner pressure of the fluid channel is fluctuated by sucking and injecting a test solution with use of a nozzle member inserted through the seal member 200, or as the operation of inserting and taking out a nozzle member with respect to the seal member 200 is repeated for sucking and injecting a test solution.

CITATION LIST

Patent Literature

Patent literature 1: WO2006/104213A
Patent literature 2: Japanese Patent No. 3,660,006

SUMMARY OF INVENTION

An object of the invention is to provide a test chip provided with a fluid channel with no or less liquid leakage when a sample solution is injected and sucked in and out of the fluid channel with use of a nozzle member such as a pipette, and a test chip unit incorporated with the test chip.

A test chip and a test chip unit incorporated with the test chip of the invention are provided with a seal member. The seal member is constituted of laminated sheet members including a first sheet member having a predetermined ductility and a predetermined elasticity capable of forming a hole therein, and a second sheet member having a lower ductility than the first sheet member. The sheet members adjoining each other are adhered to each other. The second sheet member is disposed on the inner side than the first sheet member in the sheet laminating direction. According to the invention, it is possible to provide a test chip with a fluid channel, and a test chip unit incorporated with the test chip with no or less liquid leakage when a sample solution is injected and sucked in and out of the fluid channel with use of a nozzle member such as a pipette.

These and other objects, features and advantages of the present invention will become more apparent upon reading the following detailed description along with the accompanying drawings.

BRIEF DESCRIPTION OF DRAWINGS

FIGS. 7A to 7C are diagrams describing an operation of injecting and sucking a test solution in and out of a fluid channel in the test chip, wherein FIG. 7A shows a state before a hole is formed in a seal member, FIG. 7B shows a state that a test solution is injected into the fluid channel, and FIG. 7C shows a state that a test solution is sucked out of the fluid channel;

FIGS. 8A to 8C are diagrams describing a state of the respective sheets when an insertion opening is formed in the seal member of the test chip, wherein FIG. 8A shows a state before all the sheets reach an elongation limit, FIG. 8B shows a state that a second sheet has reached an elongation limit, and FIG. 8C shows a state that all the sheets have reached an elongation limit and an insertion opening is formed;

DESCRIPTION OF EMBODIMENTS

In the following, an embodiment of the invention is described referring to the accompanying drawings.

Figure 1:
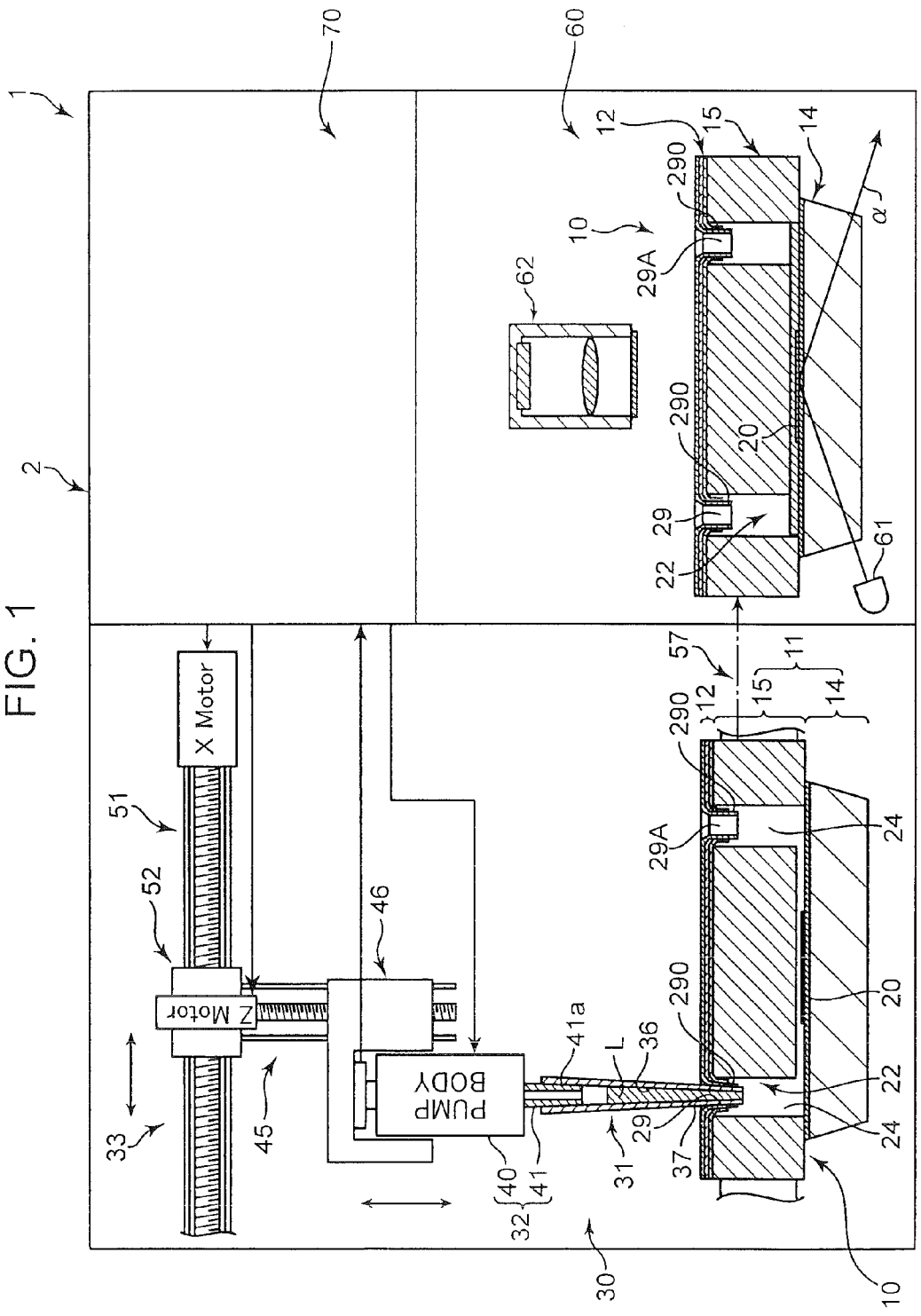
FIG. 1 is a schematic diagram of a test system embodying the invention.

A test system in this embodiment is used in a biochemical test for detecting or analyzing a sample such as an antigen, with use of a variety of test solutions. As shown in FIG. 1, the test system is provided with a test chip 10 and a test device 2. The test device 2 is configured to cause a biochemical reaction in the test chip 10 for measuring and analyzing the reaction result. The test device 2 has a liquid feeding portion (liquid feeding device) 30 for injecting and sucking a variety of test solutions L in and out of the test chip 10, a holder/carriage portion 57 for carrying the test chip 10 to a predetermined position and holding the test chip 10 at the predetermined position, a detecting portion 60 for detecting a sample and the like, and a control portion 70 for controlling the respective parts of the test device 2.

As the test solutions L in this embodiment, there are used a sample solution containing a sample to be detected, a washing solution for use in washing the inside of a fluid channel 22 of the test chip 10, and a buffer solution. The test solutions L, however, are not limited to the above. For instance, the test solutions L may include a solution containing an antibody, a solution containing a labeled antibody, a reaction suppressant solution, and other chemical solutions for use in biochemical tests.

The test chip 10 is used for testing or analyzing a biomaterial based on antigen-antibody reaction or the like. The test chip 10 in this embodiment is a sensor chip using a Kretchmann configuration. The test chip 10 is used in an analysis device for analyzing a sample based on a change in resonance angle of surface plasmon resonance, an analysis device for measuring fluorescence generated by excitation of a sample or a fluorescent substance labeled on a sample by an enhanced electric field based on surface plasmon resonance.

Figure 2A:
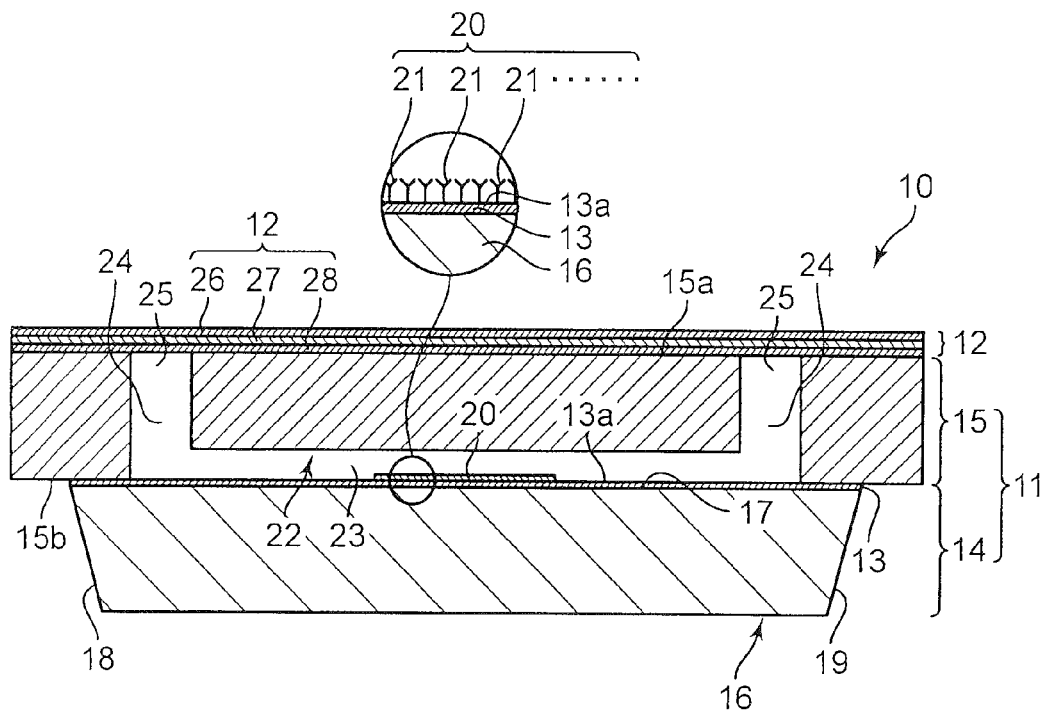
FIG. 2A is a schematic elevational sectional view of a test chip for use in the test system.

Specifically, as shown in FIG. 2A, the test chip 10 is provided with a test chip body (chip body) 11, and a seal member (elastic member) 12 for sealing an end opening (fluid channel opening) 25 of a fluid channel (solution reservoir portion) 22 formed in the test chip 10.

The test chip body 11 is provided with a prism portion 14 having a metal film 13, and a fluid channel member 15 for forming the fluid channel 22 in cooperation with the prism portion 14 for flowing a test solution L therethrough.

In the prism portion 14, surface plasmon resonance is generated on the metal film 13 by reflecting excitation light α (see FIG. 1 and FIG. 10) incident into the prism portion 14 on the metal film 13. Specifically, the prism portion 14 has a prism body portion 16 into which excitation light α for generating the aforementioned surface plasmon resonance is entered, and the metal film 13 formed on a specific surface 17 of the prism body portion 16.

The surfaces of the prism body portion 16 include an incident surface 18, a film deposition surface 17, and an exit surface 19. The prism body portion 16 is made of a transparent glass material or a transparent resin material.

The incident surface 18 is used for incidence of excitation light α from an excitation light source 61 in the detecting portion 60 into the prism body portion 16 when the test chip 10 is placed in the detecting portion 60 of the test device 2 for analyzing a sample. Further, the metal film 13 is formed on the film deposition surface 17 for reflecting excitation light α incident into the prism body portion 16. The exit surface 19 is used for outputting excitation light α reflected on the metal film 13 that has been formed on the film deposition surface 17 to the outside of the prism body portion 16.

Figure 2B:
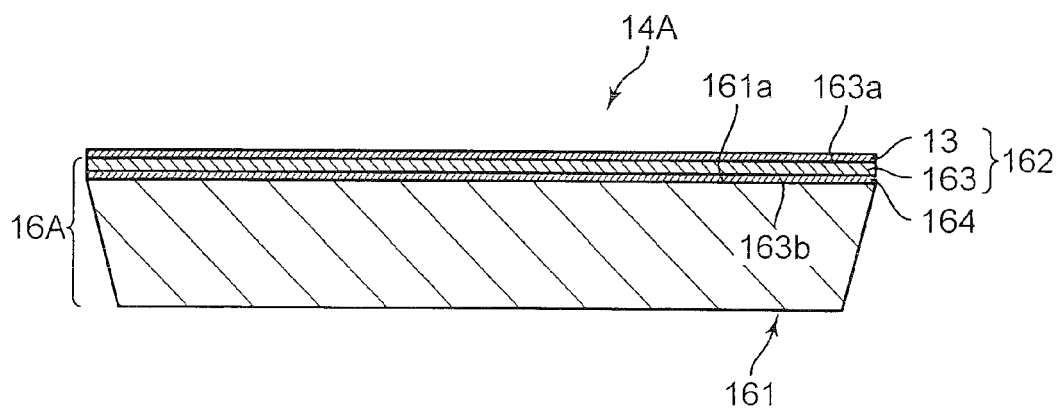
FIG. 2B is a schematic elevational sectional view of a prism body portion of a test chip as a modification.

The prism body portion 16 in this embodiment is constituted only of a prism. The prism body portion 16, however, is not limited to the above. For instance, as shown in FIG. 2B, a prism body portion 16A may have a prism 161, and a substrate portion 162 having a metal film 13 formed thereon. Specifically, a prism portion 14A is provided with the substrate portion 162 including a substrate 163 and the metal film 13 formed on the substrate 163, and the prism 161. More specifically, the substrate 163 has the same refractive index as the prism 161, and has the metal film 13 formed on a surface (one surface of the substrate 163 in the thickness direction thereof) 163a. The substrate 163 has a back surface (the other surface of the substrate 163 in the thickness direction thereof) 163b facing the prism 161, and is disposed on a specified surface 161a of the prism 161 via a matching oil 164. Thus, with use of the prism portion 14A provided with the prism 161, and the substrate portion 162 having the metal film 13 formed thereon, it is possible to keep using the prism 161 by replacing only the substrate portion 162, in the case where it is necessary to replace the metal film 13 due to peeling off, smear, or damage of the metal film 13. This is advantageous in reducing the cost.

Referring back to FIG. 2A, the metal film 13 is a thin metal film formed on the film deposition surface 17 of the prism body portion 16. The metal film 13 in this embodiment is a gold film. The metal film 13 amplifies an evanescent wave to be generated by total reflection of excitation light α from the prism body portion 16 side on the metal film 13. The metal film 13 is a thin film having a film thickness of 100 nm or smaller for generating surface plasmon resonance. Preferably, the metal film 13 is formed on the film deposition surface 17 with a film thickness of not smaller than 30 nm but not larger than 70 nm.

Further, a reaction film 20 is formed on a surface (surface of the metal film 13 on the side opposite to the prism body portion 16) 13a of the metal film 13. The reaction film 20 is formed by immobilizing biologically active substances 21 for capturing a sample (e.g. a specific antigen) contained in a sample solution (test solution) on the metal film 13. The biologically active substances 21 in the embodiment are an antibody. The biologically active substances 21 are immobilized on the surface 13a of the metal film 13 by surface treatment. Specifically, the biologically active substances 21 are immobilized in a region, on the surface 13a of the metal film 13, in contact with a sample solution flowing in the fluid channel 22. It should be noted that the biologically active substances (antibody) 21 shown in FIG. 2A are a schematic example, and the shape thereof is different from the actual shape.

The fluid channel member 15 is formed on the film deposition surface 17 (specifically, on the metal film 13) of the prism body portion 16, and forms the fluid channel 22 in cooperation with the prism portion 14. The fluid channel member 15 is made of a transparent resin material. The fluid channel member 15 in this embodiment is a plate-shaped member extending in a horizontal direction.

The fluid channel 22 has a reaction portion 23 in which a biochemical reaction (e.g. an antigen-antibody reaction) is performed, and plural (two in this embodiment) communication portions 24 for communicating between the reaction portion 23 and the outside of the test chip 10.

The reaction portion 23 is surrounded by a groove formed in a back surface (the lower surface in FIG. 2A) 15b of the fluid channel member 15, and the prism portion 14 (specifically, the metal film 13 on the prism body portion 16). Specifically, in the reaction portion 23, a sample solution flows over the surface (region where the biologically active substances 21 are immobilized) 13a of the metal film 13 in contact therewith. By the above operation, the sample solution is allowed to flow in contact with the biologically active substances 21 in flowing through the fluid channel 22. In the test chip 10 in this embodiment, reaction is promoted or stopped in the reaction portion 23, or the reaction portion 23 is washed by a test solution L (e.g. a sample solution containing a sample or a chemical solution) ejected through a nozzle member 31 of the liquid feeding portion 30. Thereafter, the sample in the sample solution that has been captured by the biologically active substances 21 is optically tested. The inner diameter of the reaction portion 23 is set smaller than the inner diameter of the communication portion 24. Specifically, the inner diameter of the reaction portion 23 is substantially equal to the size (e.g. the size in the range of from about 30 to 200 µm) capable of exhibiting a capillary phenomenon.

One end of each of the communication portions 24 is opened in a surface (upper surface in FIG. 2A) 15a of the fluid channel member 15, and the other end (end opposite to the one end) of each of the communication portions 24 is connected to the reaction portion 23. In this embodiment, the communication portions 24, 24 respectively extend from both ends of the reaction portion 23 toward the upper surface (in other words, the upper surface 15a of the fluid channel member 15) of the test chip body 11 to form openings in the upper surface (surface) 15a of the test chip body 11. In this way, the fluid channel 22 is formed by the reaction portion 23, and the paired communication portions 24 and 24.

The seal member 12 is a member in the form of a sheet. The seal member 12 brings the inside of the fluid channel 22 to a sealed state by covering the fluid channel openings 25 on the surface of the test chip body 11. The seal member 12 in this embodiment covers the entirety of the upper surface 15a of the test chip body 11. The seal member, however, is not limited to the above. Specifically, the seal member may be formed at least in a region capable of sealing the fluid channel openings 25. As long as the seal member 12 is formed in a region at least capable of sealing the fluid channel openings 25, the inside of the fluid channel 22 is sealed.

The seal member 12 is a multilayer sheet formed by laminating plural sheets. The seal member 12 is configured such that sheets adjoining each other in the laminating direction are adhered to each other. The seal member 12 in this embodiment is configured such that sheets adjoining each other in the laminating direction are adhered to each other by an adhesive or a tackifier. The seal member 12 in this embodiment has a three-layer structure. Specifically, the seal member 12 is constituted of a first sheet (first sheet member) 26, a second sheet (second sheet member) 27, and a third sheet 28 laminated one over another in this order.

Figure 3:
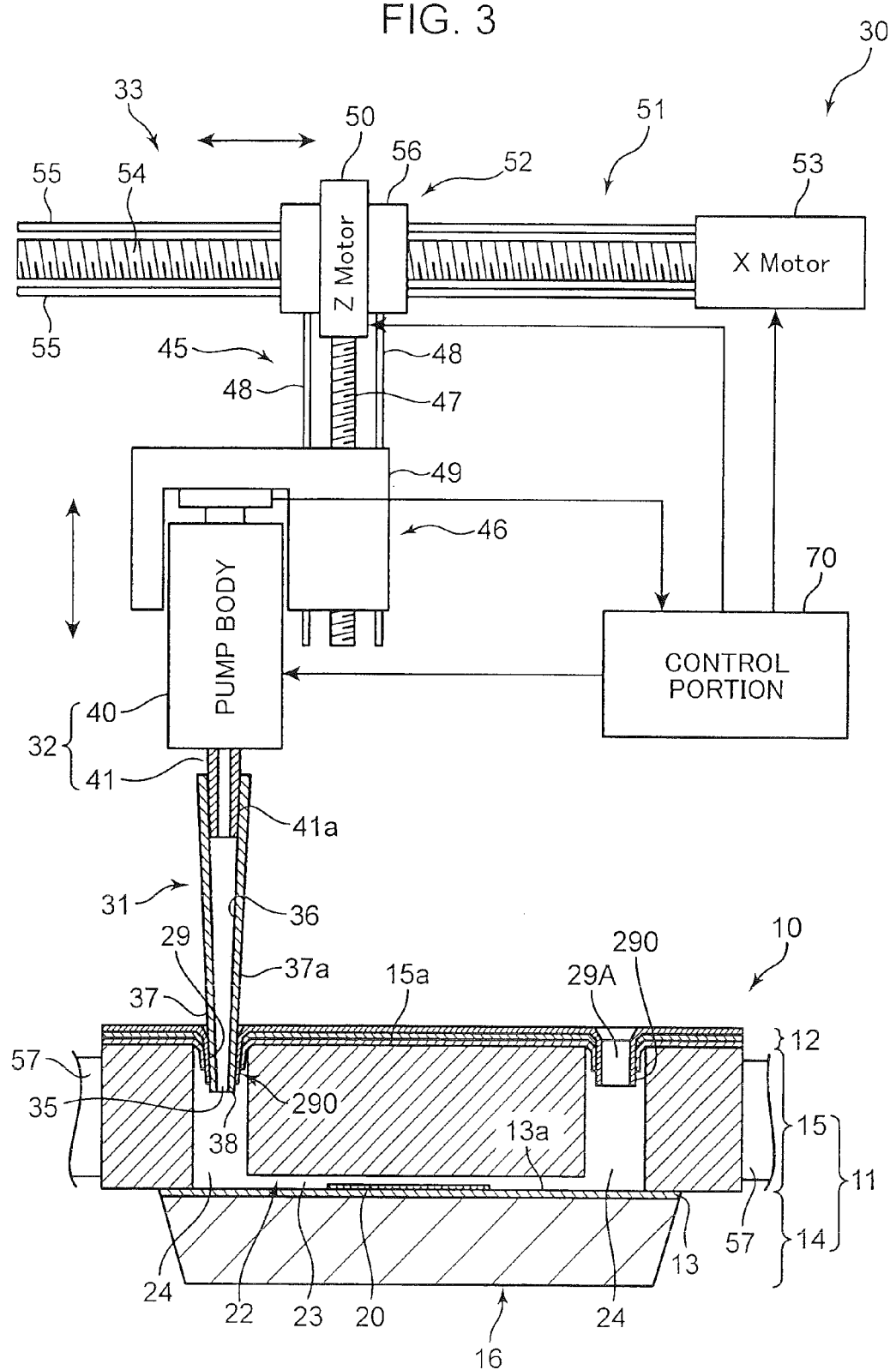
FIG. 3 is a schematic configuration diagram of a solution feeding portion and a control portion in a state that the test chip of the test system is disposed.

The first sheet 26 is a polymer film having a certain ductility and a certain elasticity (see FIG. 2A and FIG. 3). Specifically, the first sheet 26 has a ductility capable of forming a hole therein by pressing a tip of the nozzle member 31 of the liquid feeding portion 30 against the first sheet 26. The first sheet 26 has an elasticity capable of securing sufficient adhesion (sealability) between the seal member 12 and the nozzle member 31 by adhesion of a portion (i.e. an insertion opening periphery 290 of the seal member 12) surrounding the hole (insertion opening 29) formed in the seal member 12, to an outer circumferential surface 37a of the nozzle member 31. Specifically, the first sheet 26 has a low elasticity and a high ductility (for instance, the total elongation is in the range of from 200 to 720%, and the elastic modulus is in the range of from 0.05 to 0.5 Pa). The first sheet 26 in this embodiment is made of low-density polyethylene (LDPE) and has a thickness of from 30 to 70 µm. The first sheet 26 made of LDPE has a total elongation of from 480 to 720%, and an elastic modulus of from 0.19 to 0.4 Pa, for instance.

The material of the first sheet 26 is not limited to LDPE. For instance, the material of the first sheet 26 may be a polymer film having a high ductility and a low elasticity such as linear low-density polyethylene (LLDPE), copolymer of ethylene vinyl acetate (EVA), or aliphatic/aromatic copolyester. In the case where the first sheet 26 is made of LLDPE, for instance, the total elongation of the first sheet 26 is in the range of from 230 to 690%, and the elastic modulus of the first sheet 26 is in the range of from 0.17 to 0.39 Pa. Further, in the case where the first sheet 26 is made of EVA, for instance, the total elongation of the first sheet 26 is 550%, and the elastic modulus of the first sheet 26 is in the range of from 0.05 to 0.14 Pa.

The second sheet 27 is made of a material having a lower ductility than the first sheet 26 (total elongation is 50% or less). The second sheet 27 is disposed on the inner side (test chip body 11 side) than the first sheet 26 in the seal member 12. The material of the second sheet 27 in this embodiment is aluminum (AL). The second sheet 27 has a thickness of from 3 to 10 μm. The second sheet 27 made of AL has a total elongation of from 20 to 25%, and an elastic modulus of 70 Pa, for instance.

The material of the second sheet 27 is not limited to AL. For instance, the material of the second sheet 27 may be a metal (including an alloy) such as copper (Cu), tin (Sn), or gold (Au). In the case where the material of the second sheet 27 is Cu, for instance, the total elongation of the second sheet 27 is in the range of from 7 to 13%, and the elastic modulus of the second sheet 27 is 130 Pa. Further, in the case where the material of the second sheet 27 is Sn, for instance, the total elongation of the second sheet 27 is 20%, and the elastic modulus of the second sheet 27 is 50 Pa. Further, in the case where the material of the second sheet 27 is Au, for instance, the total elongation of the second sheet 27 is 42%.

In the case where the second sheet 27 is made of aluminum, it is possible to sufficiently prevent moisture intrusion and light incidence between the inside of the fluid channel 22 and the outside of the test chip 10. The second sheet 27 may be disposed further on the outer side than the first sheet 26.

The third sheet 28 is a self-adhesive film containing a tackifier. The third sheet 28 has a thickness of from 20 to 100 μm. The seal member 12 is firmly adhered to the test chip body 11 by the third sheet 28.

The seal member 12 may be adhered to the test chip body 11 by a coat-type adhesive, in place of using the third sheet (self-adhesive film) 28. The coat-type adhesive is an adhesive in the form of a liquid, sol or gel, unlike a sheet-like or film-like adhesive such as the aforementioned self-adhesive film.

The liquid feeding portion (liquid feeding device) 30 causes a biochemical reaction in the test chip 10 by injecting and sucking a test solution L in and out of the test chip 10. The liquid feeding portion 30 is provided with a nozzle member 31, a pump 32, and a nozzle driving portion 33 (see FIG. 3). Further, the liquid feeding portion 30 is provided with chemical solution containers and chemical solution chips (not shown) for storing various chemical solutions (test solutions), a waste liquid container (not shown) for discarding used test solutions L, and a pipette waste container (not shown) for discarding used nozzle members 31.

The nozzle member 31 has an opening 35 formed in a tip thereof. A test solution L is ejected (injected) and sucked in and out of the fluid channel 22 of the test chip 10 through the opening 35. The nozzle member 31 in this embodiment is a pipette chip to be detachably attached to the pump 32.

The pipette chip 31 has a liquid reservoir portion 36 formed therein. The liquid reservoir portion 36 extends upwardly from the opening 35 formed in the tip of the pipette chip 31 for storing a test solution L therein. Specifically, the pipette chip 31 is a nozzle member having a long size in up and down or vertical direction. A through-hole extending in the axis direction (up and down or vertical direction in FIG. 3) of the pipette chip 31 is formed in the pipette chip 31. The liquid reservoir portion 36 corresponds to a part of the through-hole, on the side of the opening 35 formed in the tip of the pipette chip 31 (region from the opening 35 to a tip of a pump nozzle 41 extending through the through-hole). Specifically, the liquid reservoir portion 36 in this embodiment is a portion surrounding a pillar-shaped space which communicates from the opening 35 formed in the tip of the pipette chip 31 to the pump nozzle 41 connected to the pipette chip 31.

A tip portion 37 of the pipette chip 31 has the tapered outer circumferential surface 37a, which is configured such that the outer diameter thereof is gradually reduced toward the tip thereof.

Specifically, the pipette chip 31 is made of an elastic material such as polypropylene for enhancing adhesion with respect to the seal member 12. The pipette chip 31 has a tapered shape at the tip thereof. The tapered portion is configured such that the diameter thereof is reduced at a certain ratio toward the tip thereof. In other words, the inclination angle of the tapered portion is fixed. The inclination angle is in the range of from 1° to 15° with respect to the axis direction of the pipette chip 31. Further, a tip surface 38 surrounding the opening 35 formed in the tip of the pipette chip 31 intersects perpendicularly or substantially perpendicularly with the axis of the pipette chip 31.

The pump 32 is provided with a pump body 40 for sucking and discharging a fluid, and the pump nozzle 41 for connecting the pipette chip 31 to the pump body 40. The pump body 40 is connected to the control portion 70, and is controlled by the control portion 70. The pump nozzle 41 has an outer circumferential surface 41a corresponding to the inner circumferential surface of the through-hole formed in the pipette chip 31 in shape. Accordingly, the pipette chip 31 is engaged with the pump nozzle 41 when the pump nozzle 41 is inserted into the through-hole of the pipette chip 31 from the base portion side of the pipette chip 31. In this embodiment, the pump 32 is detached from the pipette chip 31 by exerting a force on the pipette chip 31 in such a direction as to remove the pipette chip 31 from the pump nozzle 41 in the axis direction of the pipette chip 31.

The nozzle driving portion 33 moves the pipette chip 31 connected to the pump 32 up and down by moving the pump 32 up and down. Specifically, the nozzle driving portion 33 has an elevator portion 45 and a horizontal direction mover portion 51.

The elevator portion 45 moves the pipette chip 31 up and down (reciprocates the pipette chip 31 in Z-axis direction) by moving the pump 32 up and down while holding the pump 32 thereon. Specifically, the pipette chip 31 is moved up and down in a state that the tip of the pipette chip 31 faces downward (in other words, toward the upper surface of the test chip 10 in a state that the pipette chip 31 is held on the holder/carriage portion 57). More specifically, the elevator portion 45 has a linear stage 46 and a Z motor 50. The linear stage 46 is provided with a feeding screw 47, a guide member 48 extending in up and down or vertical direction, and a movable carriage 49 which engages with the feeding screw 47 and with the guide member 48 individually, while holding the pump 32 thereon to be vertically movable in a predetermined range. The Z motor 50 moves the movable carriage 49 in Z-axis direction (in other words, moves the movable carriage 49 up and down) along the guide member 48 by rotating the feeding screw 47 of the linear stage 46. The Z motor 50 is connected to the control portion 70, and is controlled by the control portion 70.

The horizontal direction mover portion 51 moves the pump 32 in a horizontal direction (in this embodiment, X-axis direction; left and right or transverse direction in FIG. 3), in other words, moves the pump 32 in a direction orthogonal to Z-axis direction. The horizontal direction mover portion 51 in this embodiment moves the pump 32 with the pipette chip 31 attached thereto and the elevator portion 45 altogether in X-axis direction. Specifically, the horizontal direction mover portion 51 is provided with a linear stage 52 and an X motor 53. The linear stage 52 is provided with a feeding screw 54, a guide member 55 extending in X-axis direction, and a movable carriage 56 which engages with the feeding screw 54 and with the guide member 55 individually, while holding the elevator portion 45 thereon. The X motor 53 moves the movable carriage 56 in X-axis direction along the guide member 55 by rotating the feeding screw 54 of the linear stage 52. The X motor 53 is connected to the control portion 70 and is controlled by the control portion 70.

The holder/carriage portion 57 carries the test chip 10, which has been placed in the test device 2 through a chip insertion port (not shown) or a like opening, to a predetermined position in the liquid feeding portion 30, while holding the test chip 10 thereon; and holds the test chip 10 at the predetermined position. In the liquid feeding portion 30, when a biochemical reaction in the fluid channel 22 of the test chip 10 is finished, the holder/carriage portion 57 carries the test chip 10 to a predetermined position in the detecting portion 60, and holds the test chip 10 at the predetermined position. The biochemical reaction in the fluid channel 22 in this embodiment is capturing a sample or the like by the biologically active substances 21 or labeling a fluorescent substance on a captured sample.

Specifically, in the liquid feeding portion 30, the holder/carriage portion 57 holds the test chip 10 in such a posture (posture shown in FIG. 3) that the fluid channel member 15 is disposed on the upper side and the prism portion 14 is disposed on the lower side. More specifically, the holder/carriage portion 57 holds the test chip 10 in such a manner that the two fluid channel openings 25 in the upper surface 15a of the test chip body 11 are respectively located beneath the moving track of the pipette chip 31 in X-axis direction. Further, the holder/carriage portion 57 holds the test chip 10 in such a manner that the fluid channel member 15 is disposed on the upper side and the prism portion 14 is disposed on the lower side in the detecting portion 60. Specifically, the holder/carriage portion 57 holds the test chip 10 at such a position that excitation light α to be emitted from the excitation light source 61 is incident into the prism portion 14 through the incident surface 18 of the prism portion 14.

The detecting portion 60 is provided with the excitation light source 61 for emitting excitation light α, and an excitation fluorescence measuring portion (measurement optical system) 62 for measuring excitation fluorescence.

The excitation light source 61 outputs excitation light α toward the prism portion 14 of the test chip 10 through the incident surface 18, and reflects the light on the metal film 13. By the above operation, plasmon resonance is generated on the metal film 13. In generating plasmon resonance, the excitation light source 61 emits excitation light α so that the excitation light α enters the metal film 13 from the back side of the region (region corresponding to the reaction portion 23 of the fluid channel 22) on the metal film 13 where the biologically active substances 21 are immobilized. In this way, an enhanced electric field generated by plasmon resonance on the metal film 13 causes the sample captured by the biologically active substances 21 or the fluorescent substance labeled on the sample to emit fluorescence.

Figure 10:
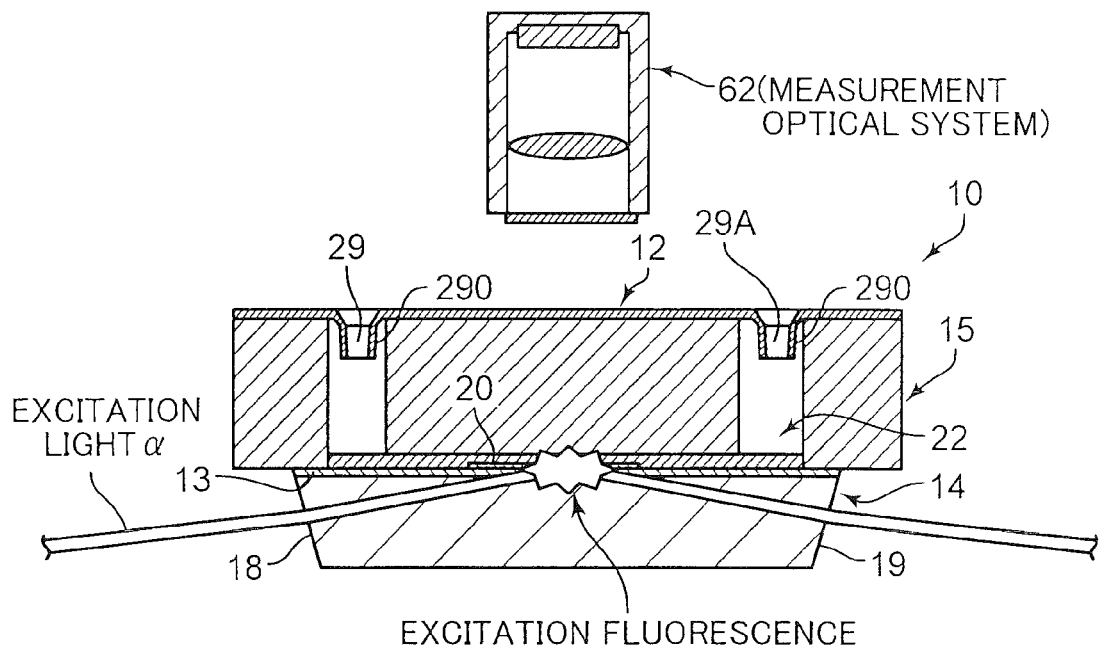
FIG. 10 is a schematic configuration diagram of a detecting portion of a test device in the test system.

The excitation fluorescence measuring portion 62 is disposed above the test chip 10 held on the holder/carriage portion 57 in the detecting portion 60 (see FIG. 1 and FIG. 10). The excitation fluorescence measuring portion 62 measures the light amount of excitation fluorescence excited by the enhanced electric field, and outputs the measurement result to the control portion 70.

The chemical solution containers, the waste liquid container, and the pipette waste container are containers configured such that upper ends of the respective containers are opened or allowed to be opened so that the pipette chip 31 can be inserted from above. The chemical solution containers, the waste liquid container, and the pipette waste container are disposed beneath the moving track of the pipette chip 31 in X-axis direction.

Figure 4:
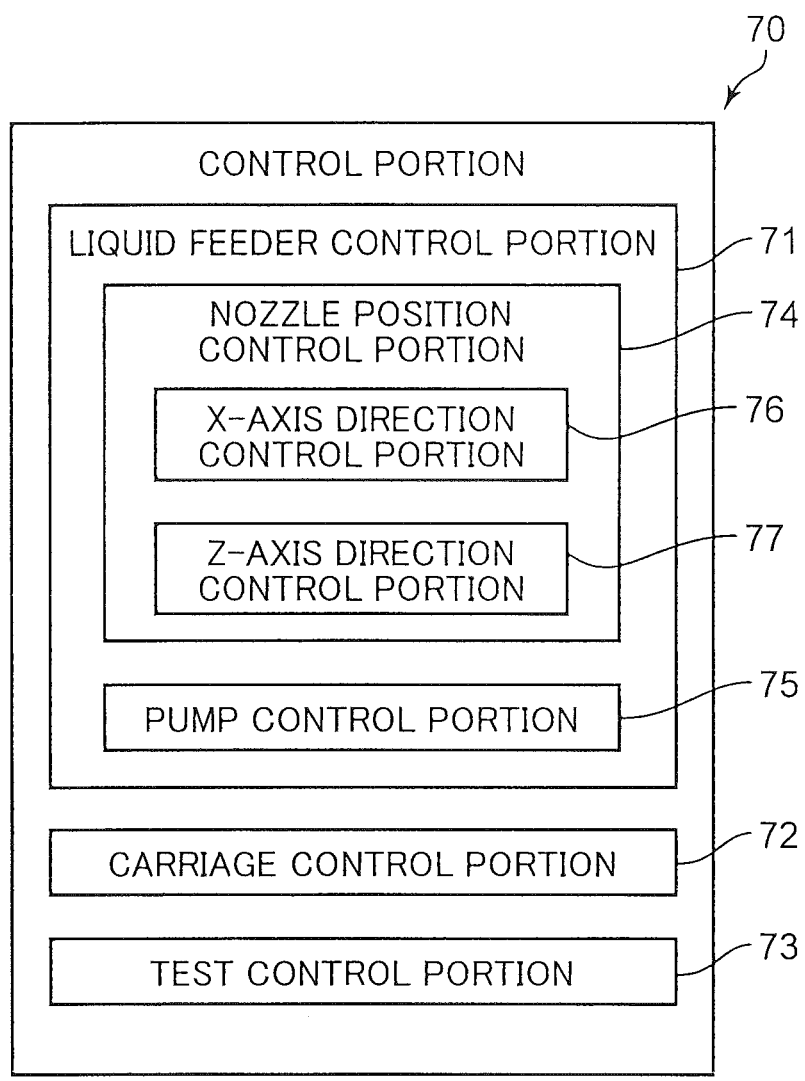
FIG. 4 is a functional block diagram of the control portion.

The control portion 70 is a circuit for controlling the respective parts of the test device 2 according to the functions of the respective parts. For instance, the control portion 70 is constituted of a microcomputer. The microcomputer is provided with: an ROM (Read Only Memory) as a non-volatile storage element or an EEPROM (Electrically Erasable Programmable Read Only Memory) as a rewritable non-volatile storage element for storing various predetermined programs, such as a control program for controlling the respective parts of the test device 2 according to the functions of the respective parts, and an operation program for detecting or analyzing a sample based on an output from the excitation fluorescence measuring portion 62, and various predetermined data such as data necessary for execution of the predetermined programs; a CPU (Central Processing Unit) for performing a predetermined arithmetic processing or control processing by reading and executing the predetermined programs; an RAM (Random Access Memory) as a working memory of the CPU for storing data generated in the course of execution of the predetermined programs; and peripheral circuits thereof. As shown in FIG. 4, the control portion 40 is functionally provided with a liquid feeder control portion 71, a carriage control portion 72, and a test control portion 73.

The liquid feeder control portion 71 has a nozzle position control portion 74 and a pump control portion 75, and controls the respective parts of the liquid feeding portion 30.

The nozzle position control portion 74 controls the position of the pipette chip 31. Specifically, the nozzle position control portion 74 controls the position of the pipette chip 31 relative to the test chip 10 held on the holder/carriage portion 57. The nozzle position control portion 74 has an X-axis direction control portion 76 for controlling the position of the pipette chip 31 in X-axis direction by controlling the horizontal direction mover portion 51, and a Z-axis direction control portion 77 for controlling the position of the pipette chip 31 in Z-axis direction by controlling the elevator portion 45.

The X-axis direction control portion 76 controls the X motor 53 of the horizontal direction mover portion 51 for moving the movable carriage 56 in X-axis direction along the guide member 55. Specifically, the X-axis direction control portion 76 controls the X motor 53 to thereby move the pipette chip 31 to the position above each of the openings of the chemical solution containers (not shown), the waste liquid container (not shown), and the pipette waste container (not shown), and to the position above each of the fluid channel openings 25 in the upper surface 15a of the test chip body 11.

The Z-axis direction control portion 77 controls the Z motor 50 of the elevator portion 45 for moving the movable carriage 49 in Z-axis direction along the guide member 48. By the above operation, the pipette chip 31 is moved up and down. Specifically, the Z-axis direction control portion 77 lifts the pipette chip 31 to such a height position (retracted position) at which the pipette chip 31 does not interfere with the test chip 10, the chemical solution containers, the waste liquid container, and the pipette waste container in moving the pipette chip 31 in X-axis direction. Then, the Z-axis direction control portion 77 lowers the pipette chip 31 when the pipette chip 31 has been moved along X-axis direction to the position above one of the openings of the chemical solution containers, the waste liquid container, and the like, or to the position above one of the fluid channel openings 25 of the test chip body 11.

Specifically, when the pipette chip 31 has been moved to the position above one of the openings of the chemical solution containers along X-axis direction, the Z-axis direction control portion 77 lowers the pipette chip 31 to a predetermined height position. By the above operation, the tip of the pipette chip 31 is inserted into a test solution L (a sample solution, a washing solution, or a buffer solution) stored in the chemical solution container. Then, after the pump control portion 75 controls the pump 32 to suck the test solution L into the pipette chip 31, the Z-axis direction control portion 77 lifts the pipette chip 31 to the retracted position.

Further, the Z-axis direction control portion 77 lowers the pipette chip 31 when the pipette chip 31 has been moved along X-axis direction to the position above the opening of the waste liquid container. The Z-axis direction control portion 77 stops the lowering of the pipette chip 31 when the tip of the pipette chip 31 has been inserted into the waste liquid container. Then, after the pump control portion 75 controls the pump 32 to eject the test solution L out of the pipette chip 31 into the waste liquid container, the Z-axis direction control portion 77 lifts the pipette chip 31 to the retracted position.

Further, the Z-axis direction control portion 77 controls to lower the pipette chip 31 when the pipette chip 31 has been moved along X-axis direction to the position above the opening of the pipette waste container. The Z-axis direction control portion 77 controls to stop the lowering of the pipette chip 31 when the tip of the pipette chip 31 has been inserted into the pipette waste container. Then, the Z-axis direction control portion 77 controls to detach the pipette chip 31 from the pump 32 by an unillustrated pipette attaching/detaching device for discarding the pipette chip 31. Thereafter, the Z-axis direction control portion 77 controls to lift the pipette chip 31 to the retracted position for attaching a new pipette chip 31 to the pump 32 by the pipette attaching/detaching device.

Further, the Z-axis direction control portion 77 controls to lower the pipette chip 31 to a predetermined position when the pipette chip 31 has been moved along X-axis direction to the position above one of the fluid channel openings 25 for injecting and sucking a test solution L in and out of the fluid channel 22 of the test chip 10, or for forming an air hole 29A in the seal member 12. By the above operation, the tip portion 37 of the pipette chip 31 is inserted into the fluid channel 22 through the fluid channel opening 25. In the case where the fluid channel opening 25 is covered by the seal member 12 before the above operation is performed, a hole is formed in the seal member 12 by pressing the tip of the pipette chip 31 against the seal member 12. By the above operation, the tip portion 37 of the pipette chip 31 is allowed to be inserted into the fluid channel 22. On the other hand, in the case where a hole has already been formed in the seal member 12 by the pipette chip 31, the tip portion 37 of the pipette chip 31 is inserted into the fluid channel 22 through the already-formed opening (insertion opening 29). Then, after the pump control portion 75 controls the pump 32 to eject and suck a test solution L with use of the pipette chip 31, the Z-axis direction control portion 77 lifts the pipette chip 31 to the retracted position.

The pump control portion 75 controls to actuate the pump 32 when the nozzle position control portion 74 has moved the pipette chip 31 to a predetermined position, or while the pipette chip 31 is moved to a predetermined position. Specifically, the pump control portion 75 actuates the pump 32 as described below.

Figure 5:
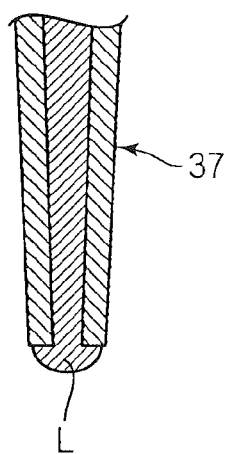
FIG. 5 is a diagram showing a state that a test solution stagnates in a tip of a nozzle member.
Figure 7A:
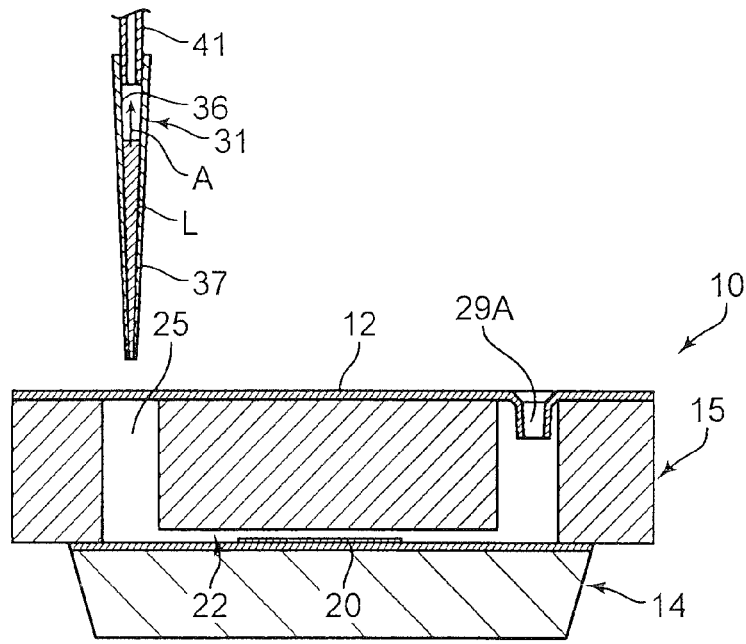
Figure 8A:
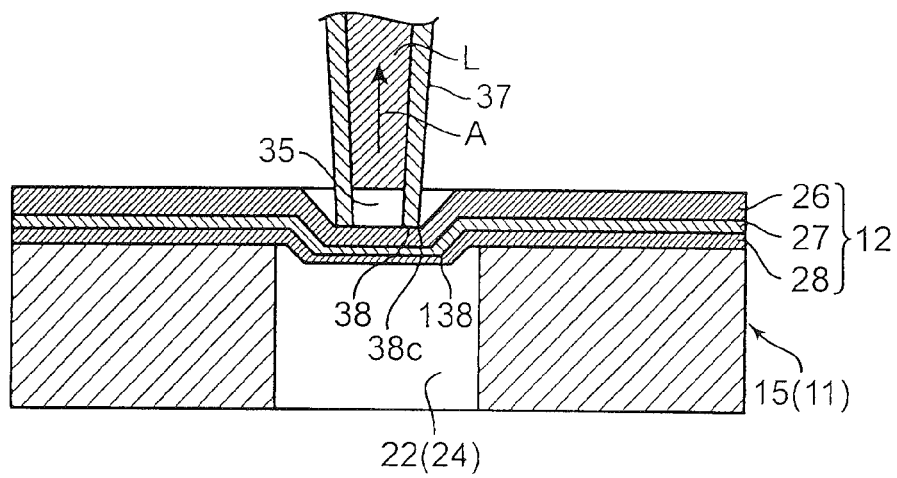

In the case where the pipette chip 31 with a test solution L being stored in the liquid reservoir portion 36 is lowered toward one of the fluid channel openings 25 of the fluid channel 22, the pump control portion 75 drives the pump 32 when the tip surface 38 of the pipette chip 31 has approached the surface (upper surface in FIG. 3) of the seal member 12 (see FIG. 7A), and controls the pump 32 to suck the test solution L out of the liquid reservoir portion 36. By the above operation, the test solution L slowly rises in the liquid reservoir portion 36. Then, when the tip portion 37 has been inserted into the fluid channel 22, and the pipette chip 31 is brought to a state that a tip of the pipette chip 31 has passed the seal member 12 to such an extent that the tip surface 38 does not come into contact with the seal member 12 (see FIG. 8C), the pump control portion 75 stops driving the pump 32 to cause the pump 32 to stop sucking the test solution L out of the liquid reservoir portion 36. In this way, during a period of time when the tip (tip surface 38) of the pipette chip 31 passes the insertion opening periphery (tubular portion) 290 of the seal member 12 in lowering the pipette chip 31, the test solution L is rising in the liquid reservoir portion 36. Accordingly, it is possible to prevent stagnation of the test solution L in the tip of the pipette chip 31 like a liquid droplet (see FIG. 5) during the above period of time (in other words, during a period of time when the tip of the pipette chip 31 passes the insertion opening periphery (tubular portion) 290 of the seal member 12 in up and down or vertical direction). The pump control portion 75 controls the pump 32 to raise the test solution L in the liquid reservoir portion 36 at such a speed that the test solution L does not intrude into the pump 32 during a period of time when the tip of the pipette chip 31 passes the seal member 12. Further, the pump control portion 75 determines timings of starting and stopping sucking of the test solution L out of the pipette chip 31, based on the position of the pipette chip 31 in Z-axis direction. The position of the pipette chip 31 in Z-axis direction may be obtained based on the amount of lowering the pipette chip 31 from the retracted position. The position of the pipette chip 31 in Z-axis direction may also be obtained from a measurement result on the position of the tip of the pipette chip 31 with use of a position sensor.

Further, in the case where the pipette chip 31 with the tip portion 37 thereof being inserted into the fluid channel 22 is lifted in a state that a test solution L is stored in the liquid reservoir portion 36, the pump control portion 75 drives the pump 32 when the tip surface 38 of the pipette chip 31 has approached the insertion opening periphery 290 of the seal member 12, and causes the pump 32 to suck the test solution L out of the liquid reservoir portion 36. By the above operation, the test solution L slowly rises in the liquid reservoir portion 36. Then, at a point of time when the pipette chip 31 has been taken out of the insertion opening 29 of the seal member 12, and the tip surface 38 of the pipette chip 31 has been lifted to a position higher than the surface of the seal member 12, the pump control portion 75 stops driving the pump 32 to stop sucking the test solution L out of the liquid reservoir portion 36 by the pump 32. By the above operation, during a period of time when the pipette chip 31 is lifted, and the tip (tip surface 38) of the pipette chip 31 passes the insertion opening periphery 290 of the seal member 12, the test solution L is rising in the liquid reservoir portion 36. Accordingly, it is possible to prevent stagnation of the test solution L in the tip of the pipette chip 31 like a liquid drop (see FIG. 5) during the above period of time (in other words, during a period of time when the tip of the pipette chip 31 passes the insertion opening periphery 290 of the seal member 12 in up and down or vertical direction). As with the case of lowering the pipette chip 31, in the aforementioned case, the pump control portion 75 controls the test solution L to rise in the liquid reservoir portion 36 at such a speed that the test solution L does not intrude into the pump 32 during a period of time when the tip of the pipette chip 31 passes the seal member 12. Further, as with the case of lowering the pipette chip 31, in the case where the pipette chip 31 is lifted, the pump control portion 75 determines timings of starting and stopping sucking of the test solution L out of the pipette chip 31, based on the position of the pipette chip 31 in Z-axis direction.

As described above, the test chip is configured such that a test solution L rises in the liquid reservoir portion 36 during a period of time when the tip of the pipette chip 31 passes the insertion opening periphery 290 of the seal member 12 in moving the pipette chip 31 up and down to thereby effectively prevent stagnation of the test solution L in the tip of the pipette chip 31 like a liquid droplet during the above period of time. Thus, it is possible to securely prevent adhesion of the test solution L in the pipette chip 31 to the insertion opening periphery 290 (seal member 12) in moving the pipette chip 31 up and down.

Further, when the tip portion 37 of the pipette chip 31 is inserted into the fluid channel 22 through the insertion opening 29, the pump control portion 75 drives the pump 32, as necessary, to inject a test solution L into the fluid channel 22, suck a test solution L out of the fluid channel 22, and repeat an operation of injecting and sucking a test solution L in and out of the fluid channel 22. By the above operation, the pump control portion 75 is operable to mix the test solutions L with each other, or promote a biochemical reaction.

Further, the pump control portion 75 drives the pump 32 to eject a test solution L (specifically, a used test solution L and the like) out of the liquid reservoir portion 36 through the pipette 31 when the tip portion 37 of the pipette chip 31 has been inserted into the waste liquid container. By the above operation, the test solution L is discarded into the waste liquid container.

The carriage control portion 72 controls the holder/carriage portion 57. Specifically, the carriage control portion 72 controls the holder/carriage portion 57 to carry the test chip 10 to a predetermined position in the liquid feeding portion 30 when the test chip 10 has been placed in the holder/carriage portion 57. When the test chip 10 has been carried to the predetermined position, the carriage control portion 72 causes the holder/carriage portion 57 to hold the test chip 10 at the predetermined position. Then, after a given process in the liquid feeding portion 30 is finished, the carriage control portion 72 causes the holder/carriage portion 57 to carry the test chip 10 to a predetermined position in the detecting portion 60. Specifically, the holder/carriage portion 57 carries the test chip 10 while keeping the posture of the test chip 10 in the liquid feeding portion 30 (posture that the fluid channel member 15 is disposed on the upper side and the prism portion 14 is disposed on the lower side). When the test chip 10 is carried to the predetermined position in the detecting portion 60, the carriage control portion 72 causes the holder/carriage portion 57 to hold the test chip 10 at the predetermined position.

The test control portion 73 controls the respective parts of the detecting portion 60, and processes a measurement result on excitation fluorescence. Specifically, when the test chip 10 has been carried to the detecting portion 60, the test control portion 73 causes the excitation light source 61 to emit excitation light α toward the test chip 10. Further, the test control portion 73 generates plasmon resonance near the metal film 13 of the test chip 10 by irradiation of excitation light α, and causes the excitation fluorescence measuring portion 62 to measure the light amount of excitation fluorescence generated by an enhanced electric field derived from the plasmon resonance. The test control portion 73 analyzes a sample, based on an output (measurement result) from the excitation fluorescence measuring portion 62. Then, the test control portion 73 outputs the analysis result to an external device (such as a display device including a monitor, or a printer) of the test device 2, or to storage means (not shown) of the test device 2.

In the thus-configured test system 1, a biochemical test is carried out as follows.

<Placing Test Chip and Air Hole Forming Step>

Figure 6:
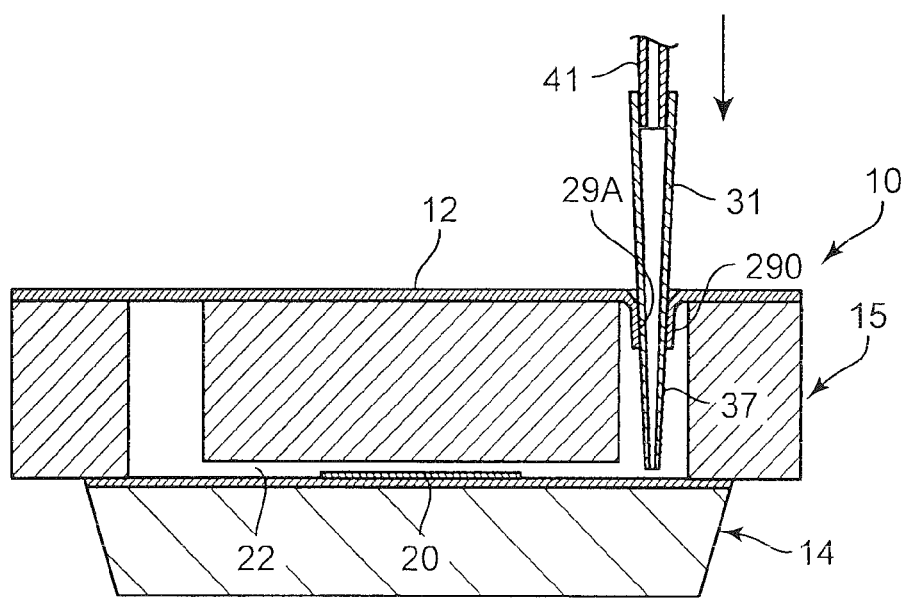
FIG. 6 is a diagram describing a method for forming an air hole in the test chip.

When the test chip 10 has been placed in the test device 2 through the chip insertion port (not shown) or a like opening, the control portion 70 controls the holder/carriage portion 57 to move the test chip 10 to the predetermined position in the liquid feeding portion 30. During the above operation, the two fluid channel openings 25 and 25 in the test chip 10 are covered by the seal member 12. Accordingly, the inside of the fluid channel 22 is in a sealed state (see FIG. 2A). When the test chip 10 is disposed at a predetermined position in the liquid feeding portion 30, the control portion 70 controls the nozzle position control portion 74 to lower the pipette chip 31. Then, the control portion 70 causes the tip portion 37 of the pipette chip 31 to penetrate through a portion of the seal member 12 which sealably covers one of the fluid channel openings 25. By the above operation, the hole (air hole) 29A for communicating between the inside of the fluid channel 22 and the outside of the test chip 10 is formed in the seal member 12 (see FIG. 6). The formation of the air hole 29A makes it easy to inject a test solution L through the other one of the fluid channel openings 25.

<Liquid Feeding Step>

The control portion 70 (specifically, the nozzle position control portion 74 and the pump control portion 75) determines the amount of test solution L (in this embodiment, a sample solution containing a sample), which is necessary for biochemical sequence in the test device 2, to be ejected from a chemical solution container into the pipette chip 31 (in other words, sucks a test solution of a predetermined amount into the liquid reservoir portion 36). Then, the nozzle position control portion 74 causes the pipette chip 31 to move to a position above the other fluid channel opening 25 (the fluid channel opening 25 sealed by the seal member 12) (see FIG. 7A). Then, the nozzle position control portion 74 controls to lower the pipette chip 31, with the sample solution being stored in the liquid reservoir portion 36, for forming a hole in the seal member 12 which seals the fluid channel opening 25, with use of the tip portion 37 of the pipette chip 31.

Specifically, when the nozzle position control portion 74 controls to lower the pipette chip 31, and the tip of the pipette chip 31 comes close to the seal member 12, the pump control portion 75 actuates the pump 32 to suck the sample solution out of the liquid reservoir portion 36. By the above operation, the sample solution slowly rises in the liquid reservoir portion 36 (see the arrow A shown in FIG. 7A). When the pipette chip 31 is further lowered by the nozzle position control portion 74, the tip surface 38 of the pipette chip 31 is abutted against the seal member 12. As the nozzle position control portion 74 continues to lower the pipette chip 31, the portion of the seal member 12 which sealably covers the other one of the fluid channel openings 25 is gradually extended while being pressed by the tip surface 38 of the pipette chip 31 (see FIG.

8A). During the above period of time, the sample solution slowly rises in the liquid reservoir portion 36. Accordingly, there is no likelihood that the sample solution may contact the seal member 12.

Figure 8B:
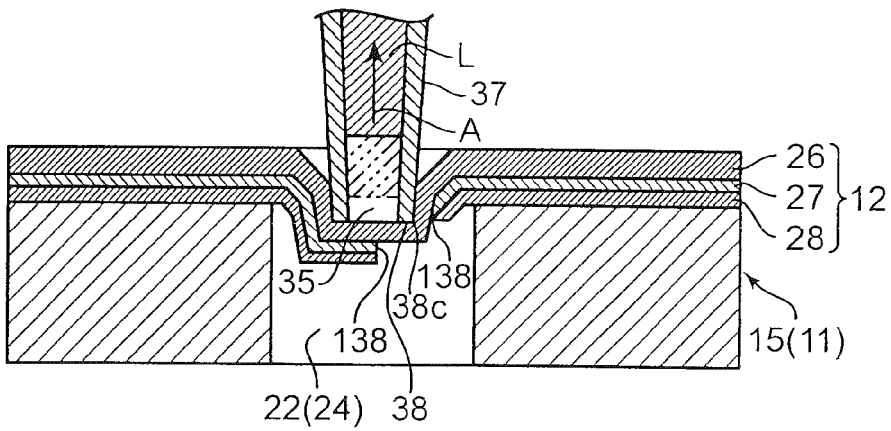
Figure 8C:
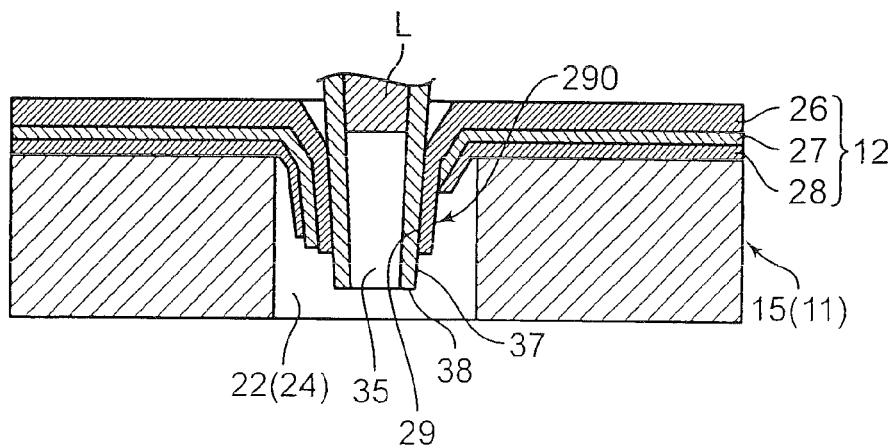

As the lowering of the pipette chip 31 continues, the second sheet 27 having a lower ductility among the sheets constituting the seal member 12 reaches an elongation limit, and starts to rupture from a position 138 corresponding to a corner portion 38c of the tip of the pipette chip 31, on which the force from the pipette chip 31 is mainly exerted (see FIG. 8B). As the pipette chip 31 is further lowered by the nozzle position control portion 74, the tip portion 37 of the pipette chip 31 is pushed into the fluid channel 22. By the above operation, a region of the first sheet 26 corresponding to the ruptured region of the second sheet 27 of the seal member 12 is extended in such a way as to adhere to the outer circumferential surface 37a of the tip portion 37 of the pipette chip 31. As a result, the tubular portion (insertion opening periphery) 290 of the seal member 12 is formed along the outer circumferential surface 37a of the tip portion 37. As the pipette chip 31 is further lowered by the nozzle position control portion 74, the first sheet 26 also reaches the elongation limit, and ruptures (see FIG. 8C). Then, the insertion opening 29 is formed in the seal member 12.

In this way, as the tip of the pipette chip 31 passes the seal member 12, the pump control portion 75 causes the pump 32 to stop sucking the sample solution out of the liquid reservoir portion 36. By the above operation, during a period of time when the tip of the pipette chip 31 passes through the insertion opening 29 in lowering the pipette chip 31, the sample solution (test solution L) rises in the liquid reservoir portion 36 of the pipette chip 31 (see FIGS. 8A to 8C). Specifically, during a period of time when the tip of the pipette chip 31 passes through the insertion opening 29, the sample solution is present in the liquid reservoir portion 36 at a position above the opening 35 formed in the tip of the pipette chip 31. This prevents stagnation of the sample solution in the tip of the pipette chip 31 like a liquid droplet. Thus, it is possible to securely prevent adhesion of the sample solution in the pipette chip 31 to the insertion opening periphery (tubular portion) 290 of the seal member 12 of the test chip 10 when the pipette chip 31 is lowered and the tip of the pipette chip 31 passes through the insertion opening 29.

Then, when the tip of the pipette chip 31 has been inserted near the reaction portion 23 of the fluid channel 22 (the position shown in FIG. 7B), the nozzle position control portion 74 controls to stop lowering the pipette chip 31. During the above operation, it is possible to obtain sufficient adhesion between the pipette chip 31 and the seal member 12, because the tubular portion (insertion opening periphery) 290 operable to adhere to the tip portion 37 (outer circumferential surface 37a) of the pipette chip 31 is formed on the first sheet 26 having a predetermined elasticity among the sheets constituting the seal member 12.

Figure 7B:
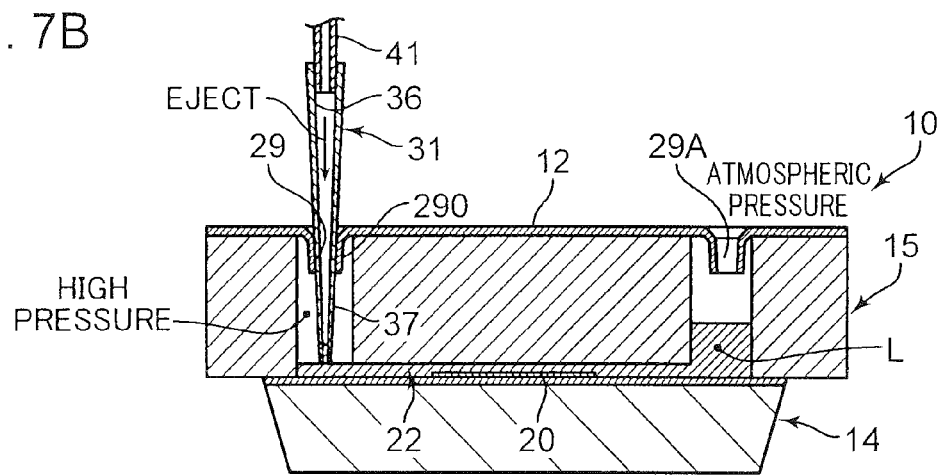
Figures 9A, 9B:
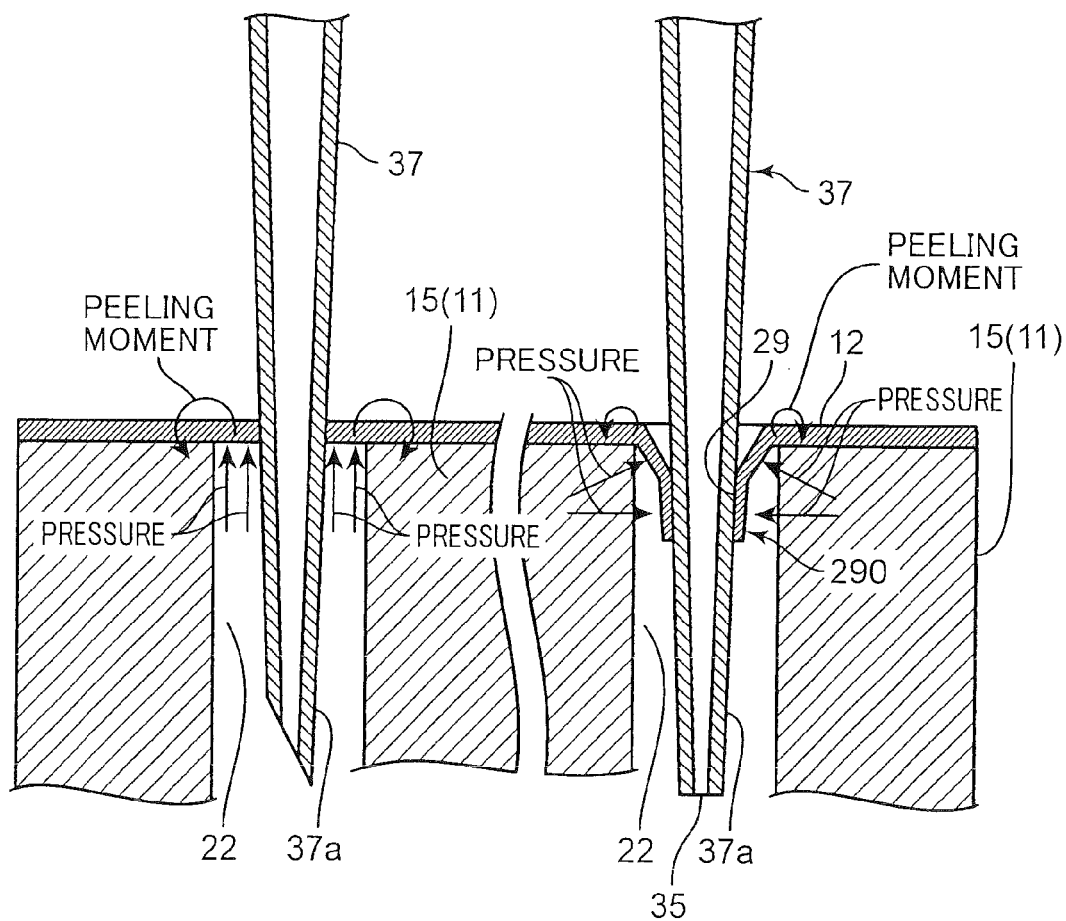
FIGS. 9A and 9B are diagrams describing an inner pressure of the fluid channel to be exerted on a periphery of the insertion opening, and a peeling moment.

Then, the pump control portion 75 causes the pump 32 to eject the sample solution out of the pipette chip 31 into the fluid channel 22 (see FIG. 7B). During the above operation, the pump control portion 75 slowly feeds the sample solution for preventing generation of air bubbles in the fluid channel 22. Then, after the fluid channel 22 (specifically, the reaction portion 23) is filled with the sample solution, the pump control portion 75 controls to increase the flow rate of the sample solution flowing in the reaction portion 23 to thereby promote the biochemical reaction between the biologically active substances 21 and the sample contained in the sample solution (capturing the sample by the biologically active substances 21). In this embodiment, the control portion 70 (pump control portion 75) controls to increase the flow rate to about 10,000 to 20,000 µL/min. Increasing the flow rate as described above may increase the inner pressure of the fluid channel 22 at a portion of the seal member 12 through which the pipette chip 31 is inserted. However, since the tubular portion (insertion opening periphery) 290 is formed out of the first sheet 26, it is possible to effectively suppress liquid leakage from between the pipette chip 31 and the seal member 12. This is because the inner pressure of the fluid channel 22 is exerted in a direction orthogonal to the planes defining the fluid channel 22. Specifically, let it be assumed that the seal member 12 is not provided with the insertion opening periphery (tubular portion) 290 when the inner pressure of the fluid channel is increased. Then, the opening periphery of the seal member 12 is likely to extend due to the inner pressure of the fluid channel, which may cause liquid leakage (see FIG. 9A). On the other hand, in the case where the insertion opening periphery 290 is formed on the seal member 12 as described above, a pressure (inner pressure of the fluid channel) is exerted on the insertion opening periphery 290 in such a direction as to press against the outer circumferential surface 37a of the pipette chip 31. Accordingly, there is no or less liquid leakage (see FIG. 9B). Further, as shown in FIGS. 9A and 9B, forming the insertion opening periphery 290 reduces a force (peeling moments shown in FIG. 9A and FIG. 9B) acting in such a direction as to peel off the seal member 12 from the test chip body 11, as compared with a configuration, in which the insertion opening periphery (tubular portion) 290 is not provided. Thus, it is possible to effectively prevent liquid leakage resulting from peeling off of the seal member 12 from the test chip body 11.

In this embodiment, the inner diameter of the reaction portion 23 (height from the metal film surface 13a shown in FIG. 2A) is in the range of from about 30 to 200 µm. Accordingly, the fluid channel resistance is large when a sample solution flows in the reaction portion 23. As a result, the inner pressure of the fluid channel 22 is higher than the atmospheric pressure (0.1 Pa) by about +0.1 Pa in terms of relative pressure. Specifically, the fluid channel resistance is determined by the shape of the fluid channel 22, the length of the fluid channel 22, the liquid feeding speed, the viscosity of the test solution L, and the like. Further, the reaction speed of biochemical reaction in the reaction portion 23 depends on the shape of the fluid channel 22 and the speed (flow rate) of the test solution L. In a biochemical test as described in this embodiment, it is preferable to set the reaction rate of biochemical reaction high by setting the inner diameter of the reaction portion 23 (height from the metal film surface 13a having the reaction film 20 formed thereon) small to such an extent that the test solution L flows exclusively near the reaction film 20 formed on the metal film 13, and by setting the flow rate of the test solution L flowing in the reaction portion 23 large. Accordingly, the fluid channel resistance of the sample solution flowing in the reaction portion 23 is made large, and this makes it possible to set the inner pressure of the fluid channel 22 (specifically, the pressure near the insertion opening 29 in which the tip portion 37 of the pipette chip 31 is inserted) high.

Figure 7C:
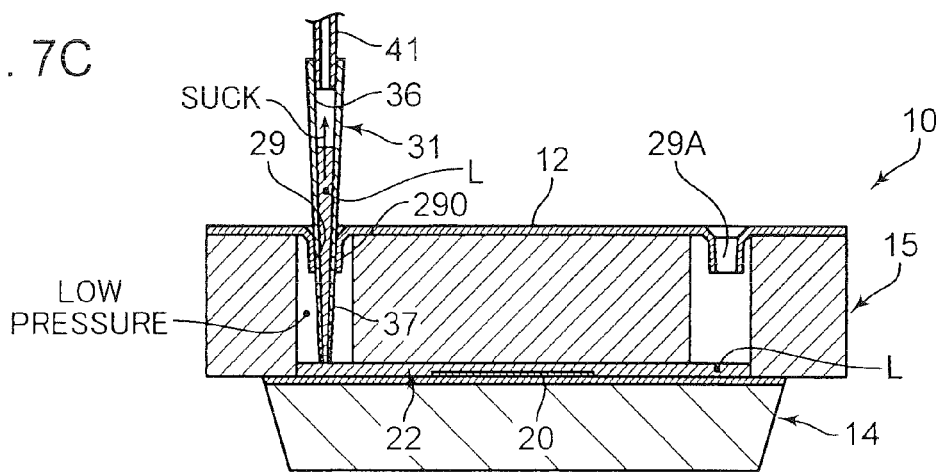

The pump control portion 75 controls the pump 32 to repeat an operation of injecting and sucking a sample solution in and out of the fluid channel 22 a certain number of times. Thereafter, the pump control portion 75 controls the pump 32 to completely suck the sample solution out of the fluid channel 22 into the pipette chip 31 (see FIG. 7C). The sucking operation is slowly performed so that there is no liquid remaining in the fluid channel 22. During a period of time when the sample solution in the fluid channel 22 is sucked, the inner pressure of the fluid channel 22 may be lowered. However, since the insertion opening periphery 290 and the pipette chip 31 are adhered to each other, it is possible to prevent intrusion of external air and the like into the fluid channel from between the insertion opening periphery 290 and the pipette chip 31. By the above operation, it is possible to efficiently suck a sample solution with use of the pipette chip 31.

When the sample solution in the fluid channel 22 is completely sucked out, the nozzle position control portion 74 controls to lift the pipette chip 31 for taking out the tip of the pipette chip 31 from the fluid channel 22 (insertion opening 29). During the above operation, as the tip of the pipette chip 31 inserted in the fluid channel 22 approaches a lower end of the insertion opening periphery (tubular portion) 290 of the seal member 12, the pump control portion 75 controls the pump 32 to suck the sample solution out of the pipette chip 31 to thereby slowly raise the sample solution in the liquid reservoir portion 36. Then, when the tip of the pipette chip 31 passes the insertion opening periphery 290, and the whole of the tip portion 37 of the pipette chip 31 is taken out of the fluid channel 22, the pump control portion 75 controls the pump 32 to stop sucking the sample solution. By the above operation, during a period of time when the tip of the pipette chip 31 passes through the insertion opening 29 in lifting the pipette chip 31, the sample solution rises in the liquid reservoir portion 36 in the pipette chip 31. Thus, it is possible to prevent stagnation of a sample solution in the tip of the pipette chip 31 like a liquid droplet in passing the pipette chip 31 through the insertion opening 29. Accordingly, it is possible to securely prevent adhesion of a sample solution in the pipette chip 31 to the insertion opening periphery (tubular portion) 290 of the test chip 10 during a period of time when the pipette chip 31 is lifted and the tip of the pipette chip 31 passes through the insertion opening 29.

When the nozzle position control portion 74 controls to move the pipette chip 31 to the waste liquid container (not shown), the pump control portion 75 controls the pump 32 to eject the used sample solution out of the pipette chip 31 into the waste liquid container.

Then, the nozzle position control portion 74 and the pump control portion 75 control the pipette chip 31 to repeat an operation of injecting and sucking other test solutions (in this embodiment, washing solutions) from the chemical solution containers (not shown) in and out of the fluid channel 22 for washing the inside of the fluid channel 22. Thereafter, the nozzle position control portion 74 and the pump control portion 75 are operated to suck all the washing solutions used in the washing step out of the fluid channel 22, and to discard all the washing solutions into the waste liquid container (not shown).

The aforementioned liquid feeding step (including the step of reacting in the reaction portion 23, and the washing step) is repeated a certain number of times. During the period of time when the above operation is repeated, the same test solution L (in this embodiment, a sample solution containing a sample) may be injected, or other test solution (for instance, a solution containing a fluorescent substance labeled on a sample captured by the biologically active substances 21 constituting the reaction film 20) may be injected and sucked.

In repeating the above liquid feeding step, an operation of inserting and taking out the tip portion 37 of the pipette chip 31 with respect to the insertion opening 29 formed in the seal member 12 is repeated. The insertion opening periphery 290 (first sheet 26) in contact with the outer circumferential surface 37a of the tip portion 37 that has been inserted into the insertion opening 29 of the seal member 12 has a predetermined elasticity as described above. Accordingly, even if the operation of inserting and taking out the tip portion 37 of the pipette chip 31 with respect to the insertion opening 29 is repeated, each time the pipette chip 31 is inserted, adhesion between the insertion opening periphery 290 and the outer circumferential surface 37a of the tip portion 37 of the pipette chip 31 is secured. Thus, it is possible to suppress liquid leakage from between the pipette chip 31 and the seal member 12 during a period of time when the test solution L is injected and sucked in and out of the fluid channel 22 with use of the pipette chip 31. Further, even if a pressure fluctuation resulting from the operation of injecting and sucking a test solution L is repeated in the fluid channel 22, formation of the insertion opening periphery 290 makes it possible to effectively suppress peeling off of the seal member 12 from the test chip body 11.

When repeating the liquid feeding step a certain number of times is finished, the nozzle position control portion 74 and the pump control portion 75 control the pipette chip 31 to inject, through the insertion opening 29, a buffer solution (other test solution) in a chemical solution container (not shown) into the fluid channel 22 from the tip portion 37 of the pipette chip 31 that has been inserted into the fluid channel 22. Then, the nozzle position control portion 74 controls to lift the pipette chip 31 in a state that the buffer solution is injected into the fluid channel 22 for taking out the tip portion 37 from the insertion opening 29. In the taking-out step, a sucking operation by the pump 32 is not performed during a period of time when the tip of the pipette chip 31 passes through the insertion opening 29. This is because a step of injecting a test solution L into the fluid channel 22 is not performed after the step of injecting a buffer solution, and accordingly, there is no possibility of contamination due to mixing of the test solutions L adhered to the insertion opening periphery 290.

After the buffer solution is injected, the nozzle position control portion 74 controls to move the pipette chip 31 to the pipette waste container (not shown). When the pipette chip 31 is moved to the pipette waste container, the pipette chip 31 is detached from the pump 32 by the pipette attaching/detaching device (not shown). By the above operation, the used pipette chip 31 is discarded into the pipette waste container. Thereafter, the Z-axis direction control portion 77 controls to lift the pipette chip 31 to the retracted position, and then, a new pipette chip 31 is attached to the pump 32 by the pipette attaching/detaching device.

<Test Step>

Next, the holder/carriage portion 57 carries the test chip 10 from the liquid feeding portion 30 to the detecting portion 60. When the test chip 10 is carried to the detecting portion 60 and is held at a predetermined position by the holder/carriage portion 57, the test control portion 73 causes the excitation light source 61 to emit excitation light α from the excitation light source 61 toward the test chip 10. By the above operation, excitation light α incident into the prism portion 14 through the incident surface 18 of the test chip 10 causes total reflection on the back side of a region (where the biologically active substances 21 are immobilized) on the metal film 13 having the reaction film 20 formed thereon. During the total reflection, the excitation light source 61 emits excitation light α toward the test chip 10 so that the excitation light α enters the metal film 13 with such an incident angle as to generate plasmon resonance on the metal film 13 (see FIG. 10). An enhanced electric field generated by the plasmon resonance excites the fluorescent substance labeled on the sample (antigen) that has been captured by the biologically active substances 21. By the above operation, the fluorescent substance emits fluorescence (excitation fluorescence). The test control portion 73 causes the excitation fluorescence measuring portion 62 to measure the light amount of emitted excitation fluorescence, and obtains the light amount of excitation fluorescence per unit area, for instance, based on the measurement result. Then, the control portion 70 outputs the obtained result to an external device (for instance, a display device such as a monitor, or a printing device such as a printer), or to storage means (not shown) of the test device 2, whereby measurement is finished.

With use of the test chip 10 and the test chip unit as described above, when the pipette chip (nozzle member) 31 is inserted through the seal member 12, adhesion (sealability) between the pipette chip 31 and the seal member 12 is sufficiently secured. Further, even if an operation of inserting and taking out the pipette chip 31 is repeated, or a pressure fluctuation in the fluid channel 22 is repeated, it is less likely that the sheets 26 and 27 constituting the seal member 12 may be peeled off from each other. Thus, it is possible to effectively prevent liquid leakage.

Further, in this embodiment, the adjoining sheets 26 and 27 are adhered to each other by an adhesive or a tackifier. This is advantageous in firmly adhering the sheets 26 and 27 to each other, as compared with a configuration, in which adjoining sheets are adhered to each other merely by thermal adhesion. Accordingly, even if a pressure fluctuation in the fluid channel 22 is repeated, or an operation of inserting and taking out the pipette chip 31 is repeated, it is less likely that the sheets 26 and 27 constituting the seal member 12 may be peeled off from each other.

Further, in this embodiment, the first sheet 26 is disposed on the outermost side among the sheets constituting the seal member 12. Accordingly, when the insertion opening periphery (tubular portion) 290 is formed by inserting the pipette chip 31 through the seal member 12, the first sheet 26 having an elasticity is contacted with the outer circumferential surface 37a of the pipette chip 31. Accordingly, the insertion opening periphery 290 is advantageously adhered to the outer circumferential surface 37a of the pipette chip 31, thereby enhancing the adhesion between the insertion opening periphery 290 and the outer circumferential surface 37a.

Further, according to this embodiment, the total elongation of the first sheet 26 is set not smaller than 200% but not larger than 720%, and the total elongation of the second sheet 27 is set not larger than 50%. Accordingly, the insertion opening periphery (tubular portion) 290 is appropriately formed when the pipette chip 31 is inserted through the seal member 12.

Further, according to this embodiment, the second sheet 27 is made of aluminum. Accordingly, it is possible to sufficiently prevent moisture intrusion and light incidence between the inside of the fluid channel 22 and the outside (outside of the test chip 10). Thus, it is possible to protect the biologically active substances 21 in the fluid channel 22 from drying or from light.

Further, in the fluid channel 22 of this embodiment, the inner diameter of an intermediate portion (reaction portion 23) is set smaller than the inner diameter of an end portion (communicating portion 24). In the thus configured fluid channel 22, when a sample solution L is injected through the fluid channel opening 25 with use of the pipette chip 31, the fluid channel resistance is increased resulting from an increase in the flow rate of the sample solution L in the reaction portion 23. As a result, the pressure around the opening 25 in the fluid channel 22 is set higher than the atmospheric pressure. In the test chip 10 provided with the thus configured fluid channel 22, use of the seal member 12 in this embodiment makes it possible to sufficiently obtain adhesion between the pipette chip 31 and the seal member 12 when the pipette chip 31 is inserted through the seal member 12. Further, even if an operation of inserting and taking out the pipette chip 31 is repeated, or a pressure fluctuation in the fluid channel 22 is repeated, it is less likely that the sheets 26 and 27 may be peeled off from each other. Thus, it is possible to effectively prevent liquid leakage.

Further, in this embodiment, it is possible to prevent adhesion of a test solution (for instance, a sample solution) L in the pipette chip 31 to the periphery 290 of the insertion opening 29 in the test chip 10 when the pipette chip 31 is moved up and down and the tip of the pipette chip 31 passes through the insertion opening 29. This is because the test solution L rises in the liquid reservoir portion 36 of the pipette chip 31 during a period of time when the tip of the pipette chip 31 passes through the insertion opening 29 in moving the pipette chip 31 up and down. This makes it possible to prevent stagnation of the test solution L in the tip of the pipette chip 31 like a liquid droplet during the above period of time.

Further, in this embodiment, during the period of time when the tip portion 37 of the pipette chip 31 is inserted in the fluid channel 22, the outer circumferential surface 37a of the tip portion 37 of the pipette chip 31 is adhered to the insertion opening periphery 290 of the seal member 12. Accordingly, it is possible to prevent liquid leakage from the insertion opening 29 in which the tip portion 37 of the pipette chip 31 is inserted, even if the inner pressure of the fluid channel 22 is fluctuated. In addition, it is possible to more effectively prevent adhesion of the test solution L to the insertion opening periphery 290 of the test chip 10, even if the diameter of the opening (insertion opening) 29 in which the pipette chip 31 is inserted is made smaller than the fluid channel opening (chip opening) 25 in the case where a seal member 12 is not provided. Specifically, the tip of the pipette chip 31 is likely to contact the insertion opening periphery 290 in inserting and taking out the pipette chip 31 with respect to the insertion opening 29. However, the test solution L in the liquid reservoir portion 36 is sucked and rises in the liquid reservoir portion 36 during a period of time when the tip of the pipette chip 31 passes through the insertion opening 29. This makes it possible to effectively prevent adhesion of the test solution L to the insertion opening periphery 290. Thus, it is possible to prevent contamination due to mixing of different test solutions L adhered to the insertion opening periphery 290 during a period of time when the test solutions L are injected and sucked in and out of the fluid channel 22.

Further, in this embodiment, the inside of the fluid channel 22 is kept in a sealed (closed) state until a test is performed by the test system 1 (in other words, until the insertion opening 29 is formed in the seal member 12). Accordingly, it is possible to securely prevent vaporization of a solution contained in the fluid channel 22 or intrusion of other substances into the solution. Further, it is possible to maintain the condition (e.g. the humidity) inside the fluid channel 22, thereby preventing contamination or drying of the biologically active substances 21 in the fluid channel 22.

Further, in this embodiment, the pipette chip 31 is detachably attached to the pump 32. Accordingly, it is easy to replace the soiled pipette chip 31 that has been used a certain number of times or used in a certain step or steps, with a clean pipette chip 31. This makes it easy to maintain the test precision. Further, use of an inexpensive pipette chip 31 such as a generic product makes it possible to suppress a cost increase, even if the frequency of replacing the pipette chip 31 is high.

The test chip and the test chip unit of the invention are not limited to the foregoing embodiment, but various modifications and/or alterations may be applied, as far as such modifications and/or alterations do not depart from the gist of the invention.

A nozzle member in this embodiment is the pipette chip 31 to be detachably attached to the pump 32 or a like member. The nozzle member, however, is not limited to the above. For instance, a nozzle member may be fixedly mounted to a pump or a like member. In other words, a nozzle member other than a disposable nozzle member as described in the embodiment may be used.

Figure 11:
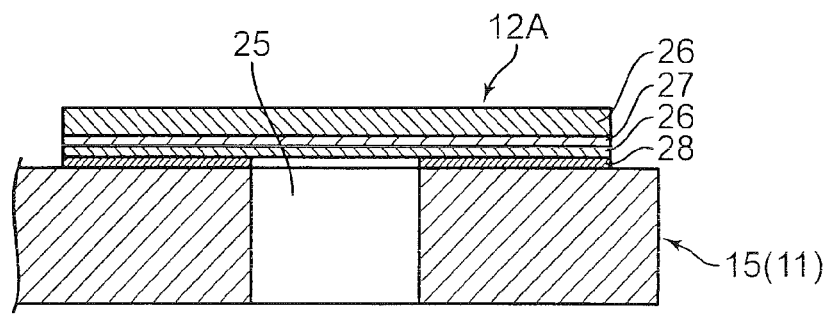
FIG. 11 is a diagram describing a seal member as another modification.
Figure 12A:
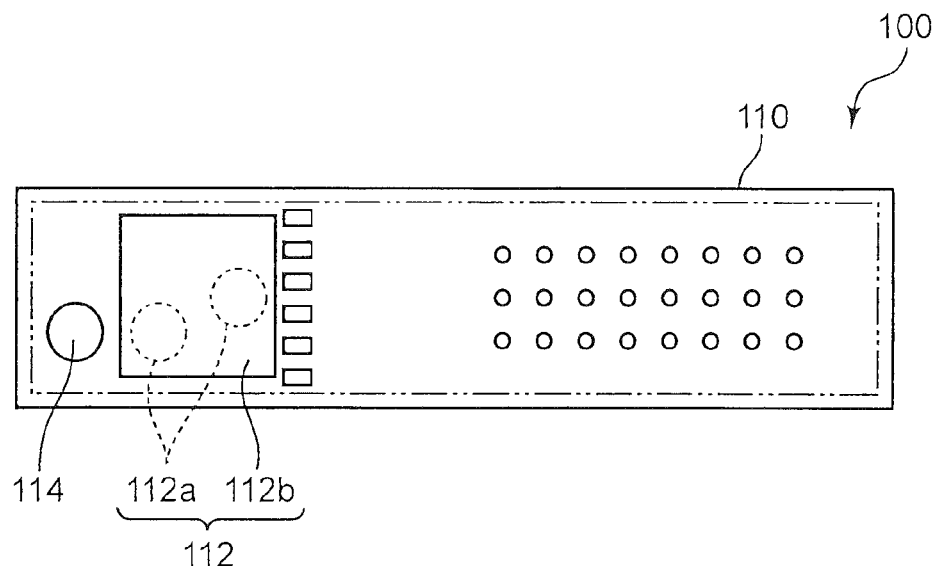
FIGS. 12A and 12B are diagrams describing a conventional test chip.
Figure 12B:
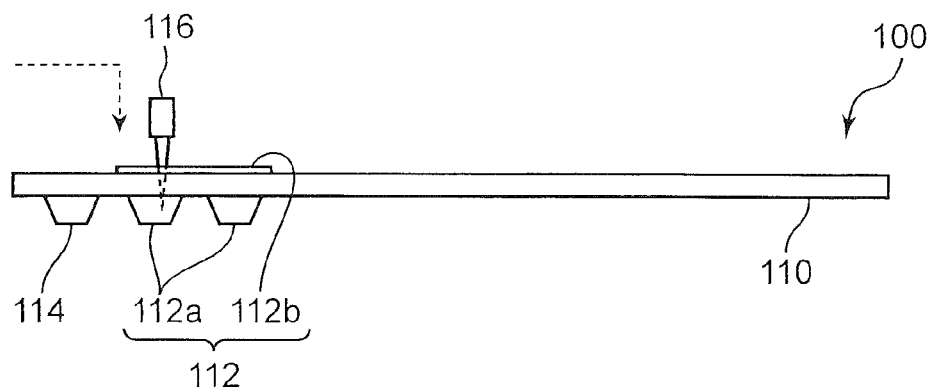
Figure 13:
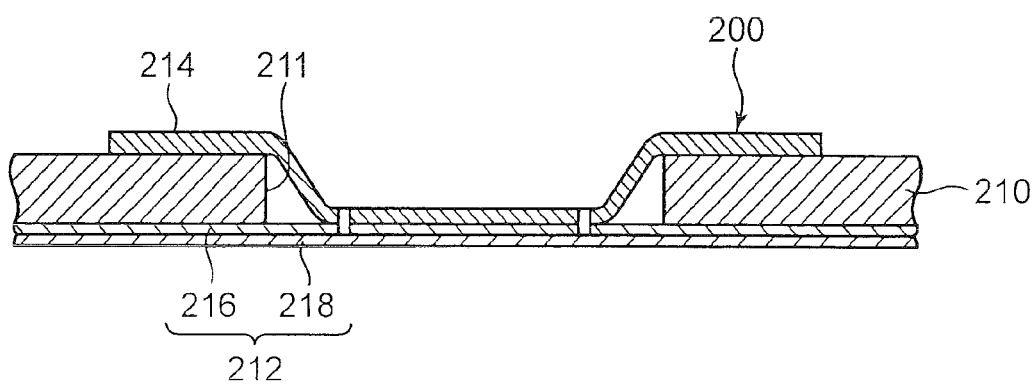
FIG. 13 is a diagram describing a seal member for use in sealing a straw insertion hole of a conventional paper beverage container.

The configuration of a seal member to be provided in the test chip 10 is not specifically limited. The seal member 12 in this embodiment has a three-layer structure, wherein the first sheet 26 having a certain ductility and a certain elasticity, the second sheet 27 having a lower ductility than the first sheet 26, and the third sheet as a self-adhesive layer are laminated one over another. The seal member, however, is not limited to the above. For instance, the seal member may be a sheet-like member constituted of two layers or more than three layers, as long as the seal member includes a first sheet and a second sheet, and the layers adjoining each other in up and down or vertical direction are adhered to each other. Specifically, as shown in FIG. 11, a seal member 12A may be configured such that a first sheet 26, a second sheet 27, a first sheet 26, and a third sheet 28 are laminated in this order. With use of the thus-configured seal member 12A, as well as the aforementioned seal member 12, the second sheet 27 starts to rupture due to a difference in ductility between the layers during a period of time when an insertion opening 29 is formed with use of a nozzle member. Further, a tubular portion (insertion opening periphery) 290 having a certain elasticity is formed out of the first sheet 26 disposed on the uppermost side in forming the insertion opening 29.

Further, in this embodiment, the first sheet 26 is disposed on the outermost side among the sheets constituting the seal member 12. The seal member, however, is not limited to the above. For instance, another sheet may be disposed on the outer side of the first sheet 26.

SUMMARY OF THE EMBODIMENT

The following is a summary of the embodiment.

A test chip according to the embodiment is a test chip for use in performing a biochemical test by injecting and sucking a test solution with use of a nozzle member. The test chip is provided with a chip body including a fluid channel having a plurality of end portions, each of the end portions of the fluid channel opened in a surface of the chip body; and a sheet-like seal member configured to cover at least the openings in the surface of the chip body for bringing an inside of the fluid channel to a sealed state. The seal member is constituted of a plurality of laminated sheet members including a first sheet member having a predetermined ductility and a predetermined elasticity capable of forming a hole therein by pressing a tip of the nozzle member against the seal member, and a second sheet member having a lower ductility than the first sheet member, the sheet members adjoining each other being adhered to each other in a direction of laminating the sheet members, and the second sheet member is disposed on an inner side than the first sheet member in the sheet laminating direction, the inner side corresponding to a side of the chip body.

According to the above configuration, when the nozzle member is inserted through the seal member, adhesion (sealability) between the nozzle member and the seal member is sufficiently secured. Further, even if an operation of inserting and taking out the nozzle member is repeated, or a pressure fluctuation in the fluid channel is repeated, it is less likely that the sheet members may be peeled off from each other. Thus, it is possible to effectively prevent liquid leakage.

Specifically, the seal member includes the first sheet member and the second sheet member having ductilities different from each other. Accordingly, when the tip of the nozzle member is pressed against the seal member, the second sheet member having a lower ductility reaches the elongation limit prior to the first sheet member. Then, the second sheet member starts to rupture from a position corresponding to a corner portion of the tip of the nozzle, on which the force from the nozzle member is mainly exerted (see FIG. 8A and FIG. 8B). As the nozzle member is further pushed into the fluid channel, a region of the first sheet member corresponding to the ruptured region of the second sheet member is extended in such a way as to adhere to the circumferential surface of the nozzle member, thereby forming a tubular portion. Then, the first sheet member also reaches the elongation limit, and ruptures (see FIG. 8C). Forming the tubular portion which adheres to the circumferential surface of the nozzle member as described above makes it possible to obtain sufficient adhesion between the nozzle member and the seal member.

Further, forming the tubular portion as described above provides sufficient durability against an increase in the inner pressure of the fluid channel. This is because the inner pressure of the fluid channel is exerted in a direction orthogonal to the planes defining the fluid channel. Let it be assumed that the seal member is not provided with the tubular portion when the inner pressure of the fluid channel is increased. Then, the opening periphery of the seal member is likely to extend due to application of a pressure to the opening periphery in such a direction as to open the opening of the seal member. This may cause liquid leakage (see FIG. 9A). On the other hand, in the case where the tubular portion of the seal member is formed as described above, a pressure is exerted on the tubular portion in such a direction as to press against the circumferential surface of the nozzle member. Accordingly, the nozzle member and the tubular portion are advantageously adhered to each other, and there is no or less liquid leakage (see FIG. 9B). Further, forming the tubular portion reduces a force acting in such a direction as to peel off the seal member from the chip body, as compared with a configuration, in which the tubular portion is not provided (see FIGS. 9A and 9B). Thus, it is possible to effectively prevent liquid leakage resulting from peeling off of the seal member from the chip body.

Preferably, the seal member may be configured such that the first sheet member is disposed on an outermost side among the sheet members. According to this configuration, when the aforementioned tubular portion is formed by inserting the nozzle through the seal member, the first sheet member having a certain elasticity is contacted with the outer circumferential surface of the nozzle member. Accordingly, the tubular portion and the outer circumferential surface of the nozzle member are advantageously adhered to each other, which enhances the sealability between the tubular portion and the nozzle member.

Specifically, satisfying the requirements that the first sheet member has a total elongation of not smaller than 200% but not larger than 720%, and the second sheet member has a total elongation of not larger than 50% makes it possible to appropriately form the tubular portion when the nozzle member is inserted through the seal member.

Further, forming the second sheet member of aluminum makes it possible to sufficiently prevent moisture intrusion and light incidence between the inside of the fluid channel and the outside of the fluid channel.

Further, the seal member may include a third sheet member having a predetermined adhesive force, and the third sheet member may be disposed at a position closest to the chip body side in the sheet laminating direction.

According to the above configuration, it is easy to adhere the seal member to the chip body. Specifically, it is possible to adhere the seal member to the chip body by the self-adhesive force of the third sheet member, without coating a coat-type adhesive (in the form of a liquid, sol or gel) on the seal member or the chip body.

Further, setting an inner diameter of a portion of the fluid channel between the end portions smaller than an inner diameter of the end portion makes it possible to set the fluid channel resistance of the test solution flowing in the fluid channel high. This makes the inner pressure near the end opening of the fluid channel higher than the atmospheric pressure when the test solution is injected through the end opening of the fluid channel with use of the nozzle member. In the test chip provided with the fluid channel as described above, use of the seal member also makes it possible to sufficiently obtain adhesion between the nozzle member and the seal member when the nozzle member is inserted through the seal member. Further, even if an operation of inserting and taking out the nozzle member is repeated, or a pressure fluctuation in the fluid channel is repeated, it is less likely that the sheet members may be peeled off from each other. Thus, it is possible to effectively prevent liquid leakage.

Further, a test chip unit according to the embodiment includes the test chip having any one of the above configurations, and a pipette chip for use in injecting and sucking a test solution in and out of the fluid channel. A tip portion of the pipette chip has a nozzle-like shape configured such that a tip of the pipette chip is opened, the pipette chip being formed into such a shape that a tip surface of the pipette chip surrounding a periphery of the opening is aligned in parallel or substantially aligned in parallel to the seal member when the tip of the pipette chip is pressed against the seal member of the test chip.

According to the above configuration, when the tip of the pipette chip is pressed against the seal member to form a hole in the seal member, the aforementioned tubular portion is securely formed. Specifically, forming a hole in the seal member with use of the pipette chip having a tip surface aligned in parallel or substantially aligned in parallel to the seal member makes it possible to extend each of the sheet members constituting the seal member while being pressed by the tip surface. This is advantageous in forming the tubular portion.

This application is based on Japanese Patent Application No. 2011-018303 filed on Jan. 31, 2011, the contents of which are hereby incorporated by reference.

INDUSTRIAL APPLICABILITY

As described above, a test chip and a test chip unit incorporated with the test chip of the invention are useful as a test chip configured such that a hole is formed in a seal member having an end opening of the test chip sealed by the seal member for injecting and sucking a test solution in and out of the fluid channel. Thus, the test chip and the test chip unit are suitable for suppressing liquid leakage when a sample solution is injected and sucked in and out of a fluid channel with use of a nozzle member such as a pipette.

The invention claimed is:

1. A test chip unit comprising a test chip for use in performing a biochemical test by injecting and sucking a test solution with use of a pipette chip, wherein:

the test chip comprises:

a chip body including a fluid channel having a plurality of end portions, each of the end portions of the fluid channel opened in a surface of the chip body; and a sheet-like seal member configured to cover at least the openings in the surface of the chip body for bringing an inside of the fluid channel to a sealed state, wherein the pipette chip is structured to inject and suck the test solution in and out of the fluid channel;

the seal member comprises a plurality of laminated sheet members including a first sheet member having a predetermined ductility and a predetermined elasticity capable of forming a hole therein by pressing a tip of the pipette chip against the seal member, and a second sheet member having a lower ductility than the first sheet member, the sheet members adjoining each other being adhered to each other in a direction of laminating the sheet members, the second sheet member is disposed on an inner side than the first sheet member in the sheet laminating direction, the inner side corresponding to a side of the chip body, the pipette chip has a tip portion in a nozzle-like shape configured such that the tip of the pipette chip is opened, the pipette chip being formed into such a shape that a tip surface of the pipette chip surrounding a periphery of the opening is aligned in parallel or substantially aligned in parallel to the seal member when the tip of the pipette chip is pressed against the seal member of the test chip, and the seal member is structured to have a tubular portion along the outer circumferential surface of the tip portion of the pipette chip when the hole is formed in the seal member with use of the tip portion of the pipette chip.

2. The test chip unit according to claim 1, wherein the seal member is configured such that the first sheet member is disposed on an outermost side among the sheet members.

3. The test chip unit according to claim 1, wherein the first sheet member has a total elongation of not smaller than 200% but not larger than 720%, and the second sheet member has a total elongation of not larger than 50%.

4. The test chip unit according to claim 1, wherein the second sheet member is made of aluminum.

5. The test chip unit according to claim 1, wherein the seal member includes a third sheet member having a predetermined adhesive force, and the third sheet member is disposed at a position closest to the chip body side in the sheet laminating direction.

6. The test chip unit according to claim 1, wherein an inner diameter of a portion of the fluid channel between the end portions is smaller than an inner diameter of the end portion.

7. The test chip unit according to claim 2, wherein the first sheet member has a total elongation of not smaller than 200% but not larger than 720%, and the second sheet member has a total elongation of not larger than 50%.

8. The test chip unit according to claim 2, wherein the second sheet member is made of aluminum.

9. The test chip unit according to claim 3, wherein the second sheet member is made of aluminum.

10. The test chip unit according to claim 2, wherein the seal member includes a third sheet member having a predetermined adhesive force, and the third sheet member is disposed at a position closest to the chip body side in the sheet laminating direction.

11. The test chip unit according to claim 3, wherein the seal member includes a third sheet member having a predetermined adhesive force, and the third sheet member is disposed at a position closest to the chip body side in the sheet laminating direction.

12. The test chip unit according to claim 4, wherein
the seal member includes a third sheet member having a predetermined adhesive force, and
the third sheet member is disposed at a position closest to the chip body side in the sheet laminating direction.

13. The test chip unit according to claim 2, wherein
an inner diameter of a portion of the fluid channel between the end portions is smaller than an inner diameter of the end portion.

14. The test chip unit according to claim 3, wherein
an inner diameter of a portion of the fluid channel between the end portions is smaller than an inner diameter of the end portion.

15. The test chip unit according to claim 4, wherein
an inner diameter of a portion of the fluid channel between the end portions is smaller than an inner diameter of the end portion.

16. The test chip unit according to claim 5, wherein
an inner diameter of a portion of the fluid channel between the end portions is smaller than an inner diameter of the end portion.

\* \* \* \* \*